United States Patent
Moraitis

(10) Patent No.: US 11,058,670 B2
(45) Date of Patent: Jul. 13, 2021

(54) THERAPEUTIC USES OF RELACORILANT, A HETEROARYL-KETONE FUSED AZADECALIN GLUCOCORTICOID RECEPTOR MODULATOR

(71) Applicant: Corcept Therapeutics Incorporated, Menlo Park, CA (US)

(72) Inventor: Andreas Moraitis, Sunny Isles Beach, FL (US)

(73) Assignee: Corcept Therapeutics Incorporated, Menlo Park, CA (US)

( * ) Notice: Subject to any disclaimer, the term of this patent is extended or adjusted under 35 U.S.C. 154(b) by 0 days.

(21) Appl. No.: 16/797,421

(22) Filed: Feb. 21, 2020

(65) Prior Publication Data

US 2020/0268723 A1   Aug. 27, 2020

Related U.S. Application Data

(60) Provisional application No. 62/809,327, filed on Feb. 22, 2019, provisional application No. 62/814,441, filed on Mar. 6, 2019, provisional application No. 62/833,517, filed on Apr. 12, 2019.

(51) Int. Cl.
*A61K 31/437* (2006.01)
*A61P 5/44* (2006.01)

(52) U.S. Cl.
CPC .............. *A61K 31/437* (2013.01); *A61P 5/44* (2018.01)

(58) Field of Classification Search
CPC ................................ A61K 31/437; A61P 5/44
See application file for complete search history.

(56) References Cited

U.S. PATENT DOCUMENTS

| | | | |
|---|---|---|---|
| 4,963,558 A | 10/1990 | Hotten et al. | |
| 5,696,127 A | 12/1997 | Jones et al. | |
| 6,583,180 B2 | 6/2003 | Link et al. | |
| 6,680,310 B2 | 1/2004 | Belanoff et al. | |
| 7,678,813 B2 | 3/2010 | Clark et al. | |
| 7,790,745 B2 | 9/2010 | Yang et al. | |
| 7,928,237 B2 | 4/2011 | Clark et al. | |
| 8,003,689 B2 | 8/2011 | Veverka | |
| 8,173,674 B2 | 5/2012 | Keil et al. | |
| 8,324,203 B2 | 12/2012 | Clark et al. | |
| 8,461,172 B2 | 6/2013 | Clark et al. | |
| 8,557,839 B2 | 10/2013 | Clark et al. | |
| 8,598,154 B2 | 12/2013 | Clark et al. | |
| 8,710,035 B2 | 4/2014 | Pan et al. | |
| 8,859,774 B2* | 10/2014 | Hunt .................. | A61K 31/5377 546/82 |
| 8,889,867 B2 | 11/2014 | Clark et al. | |
| 8,969,557 B2 | 3/2015 | Harriman et al. | |
| 9,149,485 B2 | 10/2015 | Pan et al. | |
| 9,273,047 B2 | 3/2016 | Hunt et al. | |
| 9,289,436 B2 | 3/2016 | Szmulewitz et al. | |
| 9,314,473 B2 | 4/2016 | Altschul et al. | |
| 9,422,323 B2 | 8/2016 | Houpis et al. | |
| 9,623,032 B2 | 4/2017 | Pan et al. | |
| 9,707,223 B2 | 7/2017 | Hunt et al. | |
| 9,801,893 B2 | 10/2017 | Szmulewitz et al. | |
| 9,829,495 B2 | 11/2017 | Moraitis | |
| 9,943,505 B2 | 4/2018 | Hunt et al. | |
| 9,956,216 B2 | 5/2018 | Hunt et al. | |
| 10,047,082 B2* | 8/2018 | Hunt .................... | C07D 519/00 |
| 10,117,852 B2 | 11/2018 | Hunt et al. | |
| 10,213,414 B2 | 2/2019 | Hunt et al. | |
| 10,323,034 B2 | 6/2019 | Hunt et al. | |
| 10,456,392 B2 | 10/2019 | Hunt et al. | |
| 2002/0115613 A1 | 8/2002 | Kumar | |
| 2005/0124533 A1 | 6/2005 | Schatzberg et al. | |

(Continued)

FOREIGN PATENT DOCUMENTS

| EP | 0145121 A2 | 6/1985 |
|---|---|---|
| EP | 375210 A1 | 6/1990 |

(Continued)

OTHER PUBLICATIONS

Application No. PCT/US2020/019167, International Search Report and Written Opinion, dated Jun. 19, 2020, 12 pages.
Identification of Glucocorticoid Receptor (GR) Signatures in Primary Human Breast Cancer: Association with Relapse-Free Survival Time, poster presented by S.D. Conzen as a short talk, presented at Nuclear Receptors: Signaling, Gene Regulation and Cancer, Keystone Symposia on Molecular and Cellular Biology, Keystone Resort, Keystone, Colorado, Mar. 25, 2010, 1 page.
Study of Drug 1 (Enzalutamide) Plus Drug 2 (Relacorilant) for Patients With Prostate Cancer, ClinicaiTrials.gov, Available online at: www.clinicaltrials.gov/ct2/show/NCT03674814, 9 pages.

(Continued)

*Primary Examiner* — Timothy R Rozof
(74) *Attorney, Agent, or Firm* — Kilpatrick Townsend & Stockton LLP

(57) ABSTRACT

Methods and compositions are disclosed for diagnosing a patient suspected of suffering from, and for treating a patient suffering from, a disorder such as hypercortisolemia, metabolic syndrome, pre-diabetes, diabetes, Cushing's syndrome, Cushing's Disease, hyperglycemia secondary to hypercortisolemia, a liver disease, a cardiac disorder, high blood pressure, a blood clotting disorder, a cancer, a psychological disorder, weight gain, a disorder of glucose control, a bone disorder (e.g., osteoporosis), hypogonadism, pseudoacromegaly, pituitary tumors, functional hypercortisolism, ACTH secreting tumors, peripheral neuropathy, dyslipidemia and other disorders.
The methods and compositions include administration of a heteroaryl-ketone fused azadecalin glucocorticoid receptor modulator (GRM). The preferred heteroaryl-ketone fused azadecalin GRM is relacorilant ((R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone). In some cases, the GRM (e.g., relacorilant) is orally administered. In some cases, the GRM (e.g., relacorilant) is orally administered without food.

22 Claims, 3 Drawing Sheets

(56) References Cited

U.S. PATENT DOCUMENTS

| | | |
|---|---|---|
| 2006/0063748 A1 | 3/2006 | Belanoff |
| 2006/0223852 A1 | 10/2006 | Gillespie et al. |
| 2007/0128627 A1 | 6/2007 | Simons, Jr. et al. |
| 2007/0281928 A1 | 12/2007 | Clark et al. |
| 2008/0070950 A1 | 3/2008 | Benjamin et al. |
| 2008/0287419 A1 | 11/2008 | Bruncko et al. |
| 2009/0156672 A1 | 6/2009 | Budunova et al. |
| 2010/0135956 A1 | 6/2010 | Gant et al. |
| 2010/0179115 A1 | 7/2010 | Belanoff |
| 2010/0292477 A1 | 11/2010 | Clark et al. |
| 2011/0166110 A1 | 7/2011 | Clark et al. |
| 2011/0269728 A1 | 11/2011 | Pan et al. |
| 2012/0022121 A1 | 1/2012 | Dalton et al. |
| 2012/0220565 A1 | 8/2012 | Clark et al. |
| 2013/0225633 A1 | 8/2013 | Hunt et al. |
| 2014/0038926 A1 | 2/2014 | Hunt et al. |
| 2014/0315866 A1 | 10/2014 | Pan et al. |
| 2015/0080389 A1 | 3/2015 | Hunt et al. |
| 2015/0148341 A1 | 5/2015 | Hunt et al. |
| 2017/0020860 A1 | 1/2017 | Hunt et al. |
| 2017/0273972 A1 | 9/2017 | Hunt et al. |
| 2018/0280378 A1 | 10/2018 | Hunt |
| 2019/0076424 A1 | 3/2019 | Hunt |

FOREIGN PATENT DOCUMENTS

| | | |
|---|---|---|
| EP | 375210 B1 | 5/1995 |
| EP | 3338781 A1 | 6/2018 |
| EP | 3074011 B1 | 7/2019 |
| JP | 322220 B | 4/1957 |
| JP | 04368384 A | 12/1992 |
| JP | 09505030 A | 5/1997 |
| JP | 2002506032 A | 2/2002 |
| JP | 2002544271 A | 12/2002 |
| WO | 9410150 A1 | 5/1994 |
| WO | 9504734 A1 | 2/1995 |
| WO | 9945925 A1 | 9/1999 |
| WO | 0069846 A1 | 11/2000 |
| WO | 03015692 A2 | 2/2003 |
| WO | 03061651 A1 | 7/2003 |
| WO | 2004065351 A1 | 8/2004 |
| WO | 2005087769 A1 | 9/2005 |
| WO | 2009058944 A2 | 5/2009 |
| WO | 2009064738 A2 | 5/2009 |
| WO | 2012027702 A1 | 3/2012 |
| WO | 2013177559 A2 | 11/2013 |
| WO | 2013177559 A3 | 1/2014 |

OTHER PUBLICATIONS

Study of Relacorilant in Combination with Nab-Paclitaxel for Patients with Recurrent Platinum-Resistant Ovarian, Fallopian Tube, or Primary Peritoneal Can, ClinicaiTrials.gov, Available online at: www.clinicaltrials.gov/ct2/show/NCT03776812, 11 pages.

Study to Evaluate Cort125134 in Combination with Nab-Paclitaxel in Patients with Solid Tumors, ClinicaiTrials.gov, Available online at: www.clinicaltrials.gov/ct2/show/NCT02762981, 7 pages.

Aherne, Finding the Needle in the Haystack: Why Highthroughput Screening is Good for Your Health, Breast Cancer Research, vol. 4, No. 4, 2002, pp. 148-154.

Antonarakis et al., Emerging Therapeutic Approaches in the Management of Metastatic Castration Resistant Prostate Cancer, Prostate Ca. & Prostatic Dis., vol. 14, 2011, pp. 206-218.

Attard et al., Translating Scientific Advancement into Clinical Benefit for Castration-Resistant Prostate Cancer Patients, Clin. Cancer. Res., vol. 1, Issue 12, Jun. 2011, pp. 3867-3875.

Belanoff et al., Selective Glucocorticoid Receptor {Type II) Antagonists Prevent Weight Gain Caused by Olanzapine in Rats, Eur J Pharmacol., vol. 655, Issue 1-3, Mar. 25, 2011, pp. 117-120.

Belova et al., Glucocorticoid Receptor Expression in Breast Cancer Associates with Older Patient Age, Breast Cancer Res Treat, vol. 116, Issue 3, Aug. 2009, pp. 441-447.

Benagiano et al., Selective Progesterone Receptor Modulators 3: Use in Oncology, Endocrinology and Psychiatry, Expert Opin. Pharmacother, vol. 9, No. 14, Oct. 2008, pp. 2487-2496.

Bolton et al., Cell- and Gene-Specific Regulation of Primary Target Genes by the Androgen Receptor, Genes Dev., vol. 21, No. 16, Aug. 15, 2007, pp. 2005-2017.

Chan et al., Prognostic Significance of Gleason Score 3+4 versus Gleason Score 4+3 Tumor at Radical Prostatectomy, Adult Urology, vol. 56, Issue 5, Nov. 2000, pp. 823-827.

Chen et al., Androgen and Glucocorticoid Receptor Heterodimer Formation, J. Biol. Chem., vol. 272, No. 22, May 30, 1997, pp. 14087-14092.

Chi et al., Castration-Resistant Prostate Cancer: From New Pathophysiology to New Treatment Targets, Eur. Urol., vol. 56, Issue 4, Oct. 2009, pp. 594-605.

Cho et al., Role of Activation function Domain-1, DNa Binding, and Coactivator GRIP1 in the Expression of Partial Agonist Activity of Glucocorticoid Receptor-Antagonist Complexes, Biochemistry, vol. 44, Issue 9, 2005, pp. 3547-3561.

Clark, Glucocorticoid Receptor Antagonists, Current Topics in Medicinal Chemistry, vol. 8, Issue 9, Jun. 1, 2008, pp. 813-838.

Cleutjens et al., Both Androgen Receptor and Glucocorticoid Receptor Are Able to Induce Prostate-Specific Antigen Expression but Differ in Their Growth-Stimulating Properties of LNCaP Cells, Endocrinology, vol. 138, Issue 12, Dec. 1, 1997, pp. 5293-5300.

Colleoni et al., Response to Primary Chemotherapy in Breast Cancer Patients with Tumors Not Expressing Estrogen and Progesterone Receptors, Annals of Oncology, vol. 11, Issue 8, Aug. 1, 2000, pp. 1057-1059.

Damia et al., Contemporary Pre-clinical Development of Anticancer Agents—What Are the Optimal Preclinical Models, European Journal of Cancer, vol. 45, No. 16, Nov. 2009, pp. 2768-2781.

Davies et al., Association of Glucocorticoid Receptors with Prostate Nuclear Sites for Androgen Receptors and with Androgen Response Elements, J. Mol. Endocrin., vol. 5, Issue 2, Oct. 1990, pp. 117-127.

De Bono et al., Abiraterone and Increased Survival in Metastatic Prostate Cancer, N. Engl J Med., vol. 364, No. 21, May 26, 2011, pp. 1995-2005.

Desmedt et al., Strong Time Dependence of the 76-Gene Prognostic Signature for Node-Negative Breast Cancer Patients in the Transbig Multicenter Independent Validation Series, Clinical Cancer Research, vol. 13, Issue 11, Jun. 2007, pp. 3207-3214.

Di Lorenzo et al., Castration-Resistant Prostate Cancer, Drugs, vol. 70, Issue 8, May 2010, pp. 983-1000.

Donovan et al., Androgen Receptor Expression is Associated with Prostate Cancer-Specific Survival in Castrate Patients with Metastatic Disease, BJU International, vol. 105, Issue 4, Feb. 2010, pp. 462-467.

European Patent Application No. 13751132.5, Extended European Search Report dated Mar. 21, 2016, 14 pages.

European Patent Application No. 13751132.5, Partial Supplementary European Search Report dated Sep. 7, 2015, 6 pages.

European Patent Application No. 13793417.0, Extended European Search Report dated Jan. 4, 2016, 7 pages.

European Patent Application No. 16183642.4, Extended European Search Report dated Dec. 1, 2016, 12 pages.

European Patent Application No. 18154256.4, Extended European Search Report dated Mar. 26, 2018, 6 pages.

European Patent Application No. 19188885.8, Extended European Search Report dated Oct. 28, 2019, 6 pages.

Fakih et al., Glucocorticoids and Treatment of Prostate Cancer: A Preclinical and Clinical Review, Urology, vol. 60, Issue 4, Oct. 2002, pp. 553-561.

Fiorentino et al., Blood and Tissue Biomarkers in Prostate Cancer: State of the Art, Urol Clin. North. Am., vol. 37, Issue 1, Feb. 2010, pp. 1-14.

Fradet, PSA and Beyond: Biomarkers in Prostate Cancer Diagnosis and Prognosis, Curr. Opin. Urol., vol. 19, No. 3, May 2009, pp. 243-246.

Gaddy et al., Mifepristone Induces Growth Arrest, Caspase Activation, and Apoptosis of Estrogen Receptor—Expressing, Antiestrogen-Resistant Breast Cancer Cells, Clinical Cancer Research, vol. 10, Issue 15, Aug. 1, 2004, pp. 5215-5225.

(56) References Cited

OTHER PUBLICATIONS

Genck, Chemical Processing .com, 2004.
Grover et al., The Initiation of Breast and Prostate Cancer, Carcinogenesis, vol. 23, Issue 7, Jul. 1, 2002, pp. 1095-1102.
Gulliver, Xenobiotics and the Glucocorticoid Receptor, Toxicology and Applied Pharmacology, vol. 319, Mar. 15, 2017, pp. 69-79.
Guo et al., A Novel Androgen Receptor Splice Variant is Up-Regulated During Prostate Cancer Progression and Promotes Androgen Depletion-Resistant Growth, Cancer Res., vol. 69, Issue 6, Mar. 15, 2009, pp. 2305-2313.
Han et al., Biochemical (Prostate Specific Antigen) Recurrence Probability Following Radical Prostatectomy for Clinically Localized Prostate Cancer, J. Urol., vol. 169, Issue 2, Feb. 2003, pp. 517-523.
He et al., Discovery of a Highly Potent Glucocorticoid for Asthma Treatment, Cell Discovery, vol. 1, No. 15035, 2015, 13 pages.
Hein et al., Click Chemistry, A powerful Tool for Pharmaceutical Sciences, Pharmaceutical Research, vol. 25, Issue 10, Oct. 2008, pp. 2216-2230.
Henderson et al., Estrogens as a Cause of Human Cancer: the Richard and Hinda Rosenthal Foundation Award Lecture, Cancer Research, vol. 48, Issue 2, Jan. 15, 1988, pp. 246-253.
Ho et al., A Complex Response Element in Intron 1 of the Androgen-Regulated 20-kDa Protein Gene Displays Cell Type-Dependent Androgen Receptor Specificity, J. Biol. Chem., vol. 268, No. 36, Dec. 25, 1993, pp. 27226-27235.
Huang et al., Reversal Effect of Mifepristone on Adriamycin Resistance in Human Breast Cancer Cell Line MCF-7/ADM in Vitro and in Vivo, J Cent South Univ (Med Sci), vol. 35, Issue 6, Jun. 2010, pp. 576-583.
Hunt et al., Preclinical Efficacy of the Selective GR antagonist, CORT125134, American Association for Cancer Research, 2017, 1 page.
Jemal et al., Cancer Statistics, CA: A Cancer Journal for Clinicians, vol. 60, Issue 5, Sep.-Oct. 2010, pp. 277-300.
Japanese Application No. 2007-503030, Office Action dated Feb. 23, 2011, 8 pages.
Kadmiel et al., Glucocorticoid Receptor Signaling in Health and Disease, Trends in Pharmacological Sciences, vol. 34, No. 9, Sep. 2013, pp. 518-530.
Keen et al., The Biology of Breast Carcinoma, Cancer, vol. 97, No. 3, Feb. 1, 2003, pp. 825-833.
Kim et al., Current Treatment Strategies for Castration-Resistant Prostate Cancer, Korean Journal of Urology, vol. 52, No. 3, Mar. 2011, pp. 157-165.
Klein et al., Analyzing Survival Curves at a Fixed Point in Time, Stat. Med., vol. 26, Issue 24, Oct. 30, 2007, pp. 4505-4519.
Klijn et al., Antiprogestins a New Form of Endocrine Therapy for Human Breast Cancer, Cancer Research, vol. 49, Issue 11, Jun. 1, 1989, pp. 2851-2856.
Koochekpour, Androgen Receptor Signaling and Mutations in Prostate Cancer, Asian J. Androl., vol. 12, Issue 5, Sep. 2010, pp. 639-657.
Kriaucionis et al., The Nuclear DNA Base 5-Hydroxymethylcytosine is Present in Brain and Enriched in Purkinje Neurons, Science, vol. 324, No. 5929, May 15, 2009, 5 pages.
Li et al., High Level of Androgen Receptor is Associated with Aggressive Clinicopathologic Features and Decreased Biochemical Recurrence-Free Survival in Prostate: Cancer Patients Treated with Radical Prostatectomy, Am. J. Surg. Pathol., vol. 28, No. 7, Jul. 2004, pp. 928-934.
Loi et al., Definition of Clinically Distinct Molecular Subtypes in Estrogen Receptor-Positive Breast Carcinomas Through Genomic Grade, Journal of Clinical Oncology, vol. 25, No. 10, Apr. 1, 2007, pp. 1239-1246.
Loi et al., Predicting Prognosis Using Molecular Profiling in Estrogen Receptor-Positive Breast Cancer Treated With Tamoxifen, BMC Genomics, vol. 9, No. 239, May 22, 2008, pp. 1-12.
Lotan et al., Up-Regulation of MKK4, MKK6 and MKK7 During Prostate Cancer Progression: An Important Role for SAPK Signalling in Prostatic Neoplasia, J. Pathol., vol. 212, Issue 4, Aug. 2007, pp. 386-394.
Lucci et al., Modification of Ceramide Metabolism Increases Cancer Cell Sensitivity to Cytotoxics, Int J. Onco., vol. 15 Issue 3, Sep. 1999, pp. 541-546.
Ma et al., IL-21 Activates Both Innate and Adaptive Immunity to Generate Potent Antitumor Responses that Require Perforin but are Independent of IFN-Gamma, J. Jmmunol, vol. 171, Issue 2, Jul. 15, 2003, pp. 608-615.
Makarov et al., Updated Nomogram to Predict Pathologic Stage of Prostate Cancer Given Prostate-Specific Antigen Level, Clinical Stage, and Biopsy Gleason Score (Partin Tables) Based on Cases from 2000 to 2005, Urology, vol. 69, Issue 6, Jun. 2007, pp. 1095-1101.
Melhem et al., Administration of Glucocorticoids to Ovarian Cancer Patients is Associated with Expression of the Anti-apoptotic Genes SGK1 and MKP1/DUSP1 in Ovarian Tissues, Clinical Cancer Research, vol. 15, No. 9, May 1, 2009, pp. 3196-3204.
Mikosz et al., Glucocorticoid Receptor-Mediated Protection from Apoptosis is Associated with Induction of the Serine/Threonine Survival Kinase Gene, sgk-1, The Journal of Biological Chemistry, vol. 276, No. 20, Feb. 13, 2001, pp. 16649-16654.
Minn et al., Genes that Mediate Breast Cancer Metastasis to Lung, Nature. vol. 436, No. 7050, Jul. 28, 2005, pp. 518-524.
Mohler et al., Androgen and Glucocorticoid Receptors in the Stroma and Epithelium of Prostatic Hyperplasia and Carcinoma, Clin. Cancer Res., vol. 2, Issue 5, May 1996, pp. 889-895.
Moller et al., Impact of New Technologies for Cellular Screening along the Drug Value Chain, Drug Discovery Today, vol. 14, No. 9/10, May 2010, pp. 384-390.
Moran et al., The Glucocorticoid Receptor Mediates a Survival Signal in Human Mammary Epithelial Cells, Cancer Research, vol. 60, Issue 4, Feb. 15, 2000, pp. 867-872.
Moses et al., The Growing Applications of Click Chemistry, Chem Soc Rev., vol. 36, Issue 8, May 2007, pp. 1249-1262.
Mottet et al., EAU Guidelines on Prostate Cancer. Part II: Treatment of Advanced, Relapsing, and Castration-Resistant Prostate Cancer, Eur. Urol., vol. 59, Jan. 2011, pp. 572-583.
Munster et al., A Phase 1/2 Study of Relacorilant + Nab-Paclitaxel (Nabpac) in Patients (Pts) with Solid Tumors: The Dose-Finding Phase, Journal of Clinical Oncology, vol. 36, No. 15, May 20, 2018, 4 pages.
Munster et al., A Phase 1/2 Study of Relacorilant + Paclitaxel in Patients with Solid Tumors: The Dose-Finding Phase, American Association for Cancer Research, 2018, 1 page.
Malaysian Application No. PI2014003289, Substantive Examination Adverse Report dated Mar. 30, 2018, 2 pages.
Niemeier et al., Androgen Receptor in Breast Cancer: Expression in Estrogen Receptor-Positive Tumors and in Estrogen Receptor-Negative Tumors with Apocrine Differentiation, Mod Pathol., vol. 23, No. 2, 2010, pp. 205-212.
Ocana et al., Preclined Development of Molecular-targeted Agents for Cancer, Nature Reviews Clinical Oncologyreview, vol. 8, No. 4, Apr. 2011, pp. 200-209.
Ohlmann et al., Novel Options for the Treatment of Castration-Resistant Prostate Cancer, World J. Urol., vol. 30, Issue 4, Aug. 2012, pp. 495-503.
Pan et al., Activation of the Glucocorticoid Receptor is Associated with Poor Prognosis in Estrogen Receptor-Negative Breast Cancer, Cancer Research, vol. 71, No. 20, Oct. 15, 2011, 21 pages.
Pang et al., Dexamethasone Decreases Xenograft Response to Paclitaxel Through Inhibition of Tumor Cell Apoptosis, Cancer Biology & Therapy, vol. 5, Issue 8, Aug. 2006, pp. 933-940.
International Application No. PCT/US2013/027720, International Search Report and Written Opinion dated Jun. 17, 2013, 9 pages.
International Application No. PCT/US2011/49408, International Search Report and Written Opinion dated Jan. 30, 2012, 10 pages.
International Application No. PCT/US2013/027150, International Preliminary Report on Patentability dated Sep. 4, 2014, 7 pages.
International Application No. PCT/US2013/027150, International Search Report and Written Opinion dated Apr. 29, 2013, 9 pages.

(56) References Cited

OTHER PUBLICATIONS

Peeters et al., Differential Effects of the New Glucocorticoid Receptor Antagonist ORG 34517 and RU486 (Mifepristone) on Glucocorticoid Receptor Nuclear Translocation in the AtT20 Cell Line, Ann. NY Acad. Sci., vol. 1148, Issue 1, Dec. 2008, pp. 536-541.

Petrylak et al., Evaluation of Prostate-Specific Antigen Declines for Surrogacy in Patients Treated on SWOG 99-16, J. Natl. Cancer Inst., vol. 98, Issue 8, Apr. 19, 2006, pp. 516-521.

Pike et al., Estrogens, Progestogens, Normal Breast Cell Proliferation, and Breast Cancer Risk, Epidemiologic Rev., vol. 15, Issue 1, Jan. 1, 1993, pp. 17-30.

Pound et al., Natural History of Progression after PSA Elevation Following Radical Prostatectomy, JAMA, vol. 281, No. 17, May 5, 1999, pp. 1591-1597.

Rauhala et al., Dual-Specificity Phosphatase 1 and Serum/Glucocorticoid-Regulated Kinase are Downregulated in Prostate Cancer, Int. J. Cancer, vol. 117, Issue 5, Dec. 10, 2005, pp. 738-745.

Ring et al., Mechanisms of Tamoxifen Resistance, Endocrine-Related Cancer, vol. 11, Issue 4, Dec. 2004, pp. 643-658.

Robinson et al., Octahydrophenanthrene-2,7-diol Analogues as Dissociated Glucocorticoid Receptor Agonists: Discovery and Lead Exploration, J. Med. Chem., vol. 52, No. 6, 2009, pp. 1731-1743.

Rosner et al., Higher Tumor to Benign Ratio of the Androgen Receptor mRNA Expression Associates with Prostate Cancer Progression after Radical Prostatectomy, Urology, vol. 70, Issue 6, Dec. 2007, pp. 1225-1229.

Sahoo et al., Coordinate Expression of the PI3-Kinase Downstream Effectors Serum and Glucocorticoid-Induced Kinase (SGK-1) and Akt-1 in Human Breast Cancer, European Journal of Cancer, vol. 41, Issue 17, Nov. 2005, pp. 2754-2759.

Sahu et al., FoxA1 Specifies Unique Androgen and Glucocorticoid Receptor Binding Events in Prostate Cancer Cells, Cancer Res., vol. 73, Issue 5, Mar. 2013, pp. 1570-1580.

Schenone et al., Target Identification and Mechanism of Action in Chemical Biology and Drug Discovery, Nature Chemical Biology, vol. 9, No. 4, 2013, pp. 232-240.

Scher et al., Antitumour Activity of Mdv3100 in Castration-Resistant Prostate Cancer: A Phase 1-2 Study, Lancet, vol. 375, No. 9724, Apr. 24, 2010, pp. 1437-1446.

Scher et al., Biology of Progressive, Castration-Resistant Prostate Cancer: Directed Therapies Targeting the Androgen-Receptor Signaling Axis, J Clin Oncol., vol. 23, No. 32, Nov. 10, 2005, pp. 8253-8261.

Scher et al., End Points and Outcomes in Castration-Resistant Prostate Cancer: From Clinical Trials to Clinical Practice, J. Clin. Oncol., vol. 29, No. 27, Sep. 20, 2011, pp. 3695-3704.

Schlossmacher et al., Glucocorticoid Receptor-Mediated Apoptosis: Mechanisms of Resistance in Cancer Cells, Journal of Endocrinology, vol. 211, No. 1, Oct. 2011, pp. 17-25.

Seruga et al., Drug Resistance in Metastatic Castration-Resistant Prostate Cancer, Nature Reviews Clinical Oncology, vol. 8, No. 1, Jan. 2011, pp. 12-23.

Shanmugam et al., Serum/Glucocorticoid-Induced Protein Kinase-1 Facilitates Androgen Receptor-Dependent Cell Survival, Cell Death Differ, vol. 14, No. 12, Oct. 12, 2007, pp. 2085-2094.

Sharma et al., Cell Line-based Platforms to Evaluate the Therapeutic Efficacy of Candidate Anticancer Agents, Nature Reviews Cancer, vol. 10, No. 4, Apr. 2010, pp. 241-253.

Sherk et al., Development of a Small Molecule Serum and Glucocorticoid-Regulated Kinase 1 Antagonist and its Evaluation as a Prostate Cancer Therapeutic, Cancer Res., vol. 68, Issue 18, Sep. 2008, 20 pages.

Sims et al., The Removal of Multiplicative, Systematic Bias Allows Integration of Breast Cancer Gene Expression Datasets—Improving Meta-Analysis and Prediction of Prognosis, BMC Medical Genomics, vol. 1, No. 42, Sep. 21, 2008, pp. 1-14.

Smith et al., Expression of Glucocorticoid and Progesterone Nuclear Receptor Genes in Archival Breast Cancer Tissue, Breast Cancer Research, vol. 5, Issue 1, 2003, pp. R9-R12.

Smith et al., Progesterone, Glucocorticoid, but not Estrogen Receptor mRNA is Altered in Breast Cancer Stroma, Cancer Letters, vol. 255, Issue 1, Sep. 18, 2007, pp. 77-84.

Song et al., Dihydrotestosterone Enhances Castration-Resistant Prostate Cancer Cell Proliferation through STAT5 Activation via Glucocorticoid Receptor Pathway, the Prostate, vol. 74, Issue 12, Sep. 2014, pp. 1240-1248.

Sorlie et al., Gene Expression Patterns of Breast Carcinomas Distinguish Tumor Subclasses with Clinical Implications, Proc. Nat. Acad. Sci., vol. 98, No. 19, Sep. 11, 2001, pp. 10869-10874.

Sotiriou et al., Gene Expression Profiling in Breast Cancer: Understanding the Molecular Basis of Histologic Grade to Improve Prognosis, Journal of the National Cancer Institute, vol. 98, No. 4, Feb. 15, 2006, pp. 262-272.

Srinivas et al., Phase II Study Evaluating Oral Triamcinolone in Patients with Androgen-Independent Prostate Cancer, Adult Urology, vol. 67, No. 5, May 1, 2006, pp. 1001-1006.

Srinivas et al., Proteomics for Cancer Biomarker Discovery, Clinical Chemistry, vol. 48, Issue 8, Aug. 2002, pp. 1160-1169.

Stephenson et al., Preoperative Nomogram Predicting the 10-Year Probability of Prostate Cancer Recurrence After Radical Prostatectomy, J. Natl. Cancer Inst., vol. 98, No. 10, May 17, 2006, 7 pages.

Sterbis et al., Higher Expression of the Androgen-Regulated Gene PSA-HK3 mRNA in Prostate Cancer Tissues Predicts Biochemical Recurrence-Free Survival, Clin. Cancer Res., vol. 14, Issue 3, Feb. 2008, pp. 758-763.

Stringer-Reasor et al., Glucocorticoid Receptor Activation Inhibits Chemotherapy-Induced Cell Death in High-Grade Serous Ovarian Carcinoma, Gynecologic Oncology, vol. 138, No. 3, Sep. 2015, pp. 656-662.

Sui et al., Estrogen Receptor α Mediates Breast Cancer Cell Resistance to Paclitaxel through Inhibition of Apoptotic Cell Death, Cancer Research, vol. 67, Issue 11, Jun. 1, 2007, pp. 5337-5344.

Sun et al., Castration Resistance in Human Prostate Cancer is Conferred by a Frequently Occurring Androgen Receptor Splice Variant, J Clin Invest., vol. 120, Issue 8, Aug. 2, 2010, pp. 2715-2730.

Sundahl et al., Selective Glucocorticoid Receptor-Activating Adjuvant Therapy in Cancer Treatments, Oncoscience, vol. 3, No. 7-8, Jul. 2016, pp. 188-202.

Szmulewitz et al., Serum/Glucocorticoid-Regulated Kinase 1 Expression in Primary Human Prostate Cancers, Prostate, vol. 72, Issue 2, Feb. 1, 2018=2, pp. 157-164.

Tannock et al., Docetaxel Plus Prednisone or Mitoxantrone Plus Prednisone for Advanced Prostate Cancer, The New England Journal of Medicine, vol. 351, No. 15, Oct. 7, 2004, pp. 1502-1512.

Taplin et al., A Phase II Study of Mifepristone (Ru-486) in Castration-Resistant Prostate Cancer, with a Correlative Assessment of Androgen-Related Hormones, BJU International, vol. 101, Issue 9, May 1, 2008, pp. 1084-1089.

Tessier et al., Serum and Glucocorticoid-Regulated Protein Kinases: Variations on a Theme, Journal of Cellular Biochemistry, vol. 98, Issue 6, Aug. 15, 2006, pp. 1391-1407.

Twiddy et al., Cholesterol as a Potential Target for Castration-Resistant Prostate Cancer, Pharm. Res., vol. 28, Issue 3, Mar. 2011, pp. 423-437.

Venkatesh et al., Role of the Development Scientist in Compound Lead Selection and Optimization, Journal of Pharmaceutical Sciences, vol. 89, Issue 2, Feb. 2000, pp. 145-154.

Wang et al., Gene-Expression Profiles to Predict Distant Metastasis of Lymph-Node-Negative Primary Breast Cancer, The Lancet, vol. 365, Issue 9460, Feb. 19-25, 2005, pp. 671-679.

Ward et al., Rising Prostate-Specific Antigen after Primary Prostate Cancer Therapy, Nat. Clin. Pract. Urol., vol. 2, No. 4, Apr. 1, 2005, pp. 174-182.

Wright et al., Differences in Prostate Cancer Outcomes Between Cases With Gleason 4+3 and Gleason 3+4 Tumors in a Population Based Cohort, J. Urol., vol. 182, Issue 6, Dec. 2009, pp. 2702-2707.

Wu et al., Glucocorticoid Receptor Activation Signals through Forkhead Transcription Factor 3a in Breast Cancer Cells, Mol. Endocrinol, vol. 20, No. 10, Oct. 1, 2006, pp. 2304-2314.

(56) References Cited

OTHER PUBLICATIONS

Wu et al., Microarray Analysis Reveals Glucocorticoid-Regulated Survival Genes that are Associated with Inhibition of Apoptosis in Breast Epithelial Cells, Cancer Research, vol. 64, Issue 5, Mar. 1, 2004, pp. 1757-1764.

Wu et al., Prevalent Expression of the Immunostimulatory MHC Class I Chain-Related Molecule Is Counteracted by Shedding in Prostate Cancer, J. Clin. Invest., vol. 114, Issue 4, Aug. 16, 2004, pp. 560-568.

Yemelyanov et al., Differential Targeting of Androgen and Glucocorticoid Receptors Induces ER Stress and Apoptosis in Prostate Cancer Cells, Cell Cycle, vol. 11, Issue 2, Jan. 15, 2012, pp. 395-406.

Yemelyanov et al., Tumor Suppressor Activity of Glucocorticoid Receptor in the Prostate, Oncogene, vol. 26, No. 13, Mar. 22, 2007, pp. 1885-1896.

Zegarra-Moro et al., Disruption of Androgen Receptor Function Inhibits Proliferation of Androgen-refractory Prostate Cancer Cells, Cancer Res., vol. 62, Issue 4, Feb. 2002, pp. 1008-1013.

Zou et al., Androgen-Induced Coactivator Ancca Mediates Specific Androgen Receptor Signaling in Prostate Cancer, Cancer Res., vol. 69, Issue 8, Apr. 2009, pp. 3339-3346.

Amorphous Materials: How Some Solids Flow Like Liquids, Science Daily, CNRS, Available online at: http://www.sciencedaily.com/releases/2008/07/080704153507.htm, Jul. 7, 2008, pp. 1.

Database Crossfire Beilstein; Beilstein Institut Zur Foerderung der Chemischen Wissenschaft, Accession No. 101172-52-5 (BRN), Jun. 27, 1988, 3 pages.

Definition of Amorphous Solid, Wikipedia, Jan. 16, 2014, pp. 1-3.

Barth et al., Structural and Stereoelectronic Requirements for the Inhibition of Mammalian 2,3-Oxidosqualene Cyclase by Substituted Isoquinoline Derivatives, J. Med. Chem., vol. 39, No. 12, American Chemical Society, Jun. 7, 1996, pp. 2302-2312.

Christoffers et al., Absolute Configuration of Methyl (+)-1,2,3,4,6,7,8,8a-Octahydro-6-isoquinolone-8a-carboxylate and Stereochemistry of a Copper-Catalyzed Asymmetric Michael Reaction, Zeitschrift Fuer Naturforschung B Chemical Sciences, vol. 59, Issue 4, Apr. 1, 2004, pp. 375-379.

Christoffers et al., Copper-Catalyzed Asymmetric Michael Reactions with α-Amino Acid Amides: Synthesis of an Optically Active Piperidine Derivative, Wiley Online Library, vol. 2002, Issue 9, May 2002, pp. 1505-1508.

Christoffers et al., Synthesis of an Optically Active Decahydro-6-lsoquinolone Scaffold with a Quaternary Stereocenter, Wiley Online Library, vol. 2004, Issue 12, Jun. 2004, pp. 2701-2706.

Christoffers, Transformation of an Optically Active Decahydro-6-isoquinolone Scaffold: Perfect Felkin-Anh Diastereoselectivity, Organic Letters, vol. 6, No. 7, American Chemical Society, Feb. 3, 2004, pp. 1171-1173.

Chu, STN-12691012, Connecting via Winsock to SIN at pto-stn on port 23, STN International, Mar. 19, 2012, 62 pages.

Chu et al., Successful Long-Term Treatment of Refractory Cushing's Disease with High-Dose Mifepristone (RU 486), The Journal of Clinical Endocrinology & Metabolism, vol. 86, Issue 8, Aug. 2001, pp. 3568-3573.

Clark et al., 1H-Pyrazolo[3,4-g]Hexahydro-Isoquinolines as Selective Glucocorticoid Receptor Antagonists with High Functional Activity, Bioorganic & Medical Chemistry Letters, vol. 18, Issue 4, Feb. 15, 2008, pp. 1312-1317.

Clark et al., Solid Forms and Process for Preparing, Declaration Under 37 CFR 1.132 by Robin Clark, U.S. Appl. No. 12/777,340, filed Feb. 2013, 5 pages.

Dibas et al., Glucocorticoid Therapy and Ocular Hypertension, European Journal of Pharmacology, vol. 787, Sep. 15, 2016, 33 pages.

Elmore, Nonsteroidal Selective Glucocorticoid Modulatores: The Effect of C-5 Alkyl Substitution on the Transcriptional Activation/Repression Profile of 2,5-Dihydro-10-Methoxy-2,2,4-Trimethyl-1H-[1]Benzopyrano[3,4-f]Quinolines, American Chemical Society, J. Med. Chem., vol. 44, No. 25, Dec. 1, 2001, pp. 4481-4491.

Gasparini et al., Peripheral Markers in Testing Pathophysiological Hypotheses and Diagnosis Alzheimer's Disease, FASEB. J. 12, 1998:17-34.

Gauthier et al., Alzheimer's Disease: Current Knowledge, Management and Research, Can. Med. Assoc. J. 1997; 157(8): 1047-1052.

Genck, Make the Most of Antisolvent Crystallization; A Number of Factors Can Affect Solids' Formation, Available online at: https://www.chemicalprocessing.com/articles/2010/210/, Nov. 8, 2010, 8 pages.

Greicius et al., Presenile Demential Syndrome: An Update on Taxonomy and Diagnosis, Journal of Neurosurg. Psychiatry, 2002, 72:691-700.

Gupta et al., Studies on Carboxylation in Heterocyclic Systems, J. Sci. Industr., Res., vol. 20B, Aug. 1961, pp. 394-397.

Highlights of Prescribing Information, KORLYM® (mifepristone), Corcept Therapeutics Incorporated, 2017, 7 pages.

Hsin et al., Stereoselective Synthesis of Morphine Fragments Trans- and Cisoctahydro- 1H-Benzo[4,5]Furo[3,2- e]Isoquinolines, Elsevier Ltd., Tetrahedron, vol. 61, Issue 2, Jan. 10, 2005, pp. 513-520.

Hunt, Curriculum Vitae, 4 pages.

Hunt et al., Identification of the Clinical Candidate (R)-(1-(4-Fluorophenyl)-6-((1-methyl-1H-pyrazol-4-y)sulfonyl)- 4,4a,5,6,7,8-hexahydro-1H-pyrazolo[3,4-g]isoquinolin-4a-yl)(4-(trifluoromethyl)pyridin-2-yl)methanone (CORT125134): A Selective Glucocorticoid Receptor, Journal of Medicinal Chemistry, vol. 60, No. 8, Apr. 3, 2017, pp. 3405-3421.

Johnson et al., Relationships Between Drug Activity in NCI Preclinical in Vitro and in Vivo Models and Early Clinical Trials, British Journal of Cancer, vol. 84, No. 10, May 18, 2001, pp. 1424-1431.

Kugita, Studies on the Syntheses of Hydrogenated Quinolines and Isoquinolines as Analgesics, Pharmaceutical Bulletin, vol. 4, No. 1, Feb. 1956, pp. 29-34.

Magee et al., Construction of Cis- and Trans-Decahydroisoquinolines via Heterogeneous Catalytic Hydrogenation, J. Org. Chem., American Chemical Society, vol. 64, No. 7, Mar. 16, 1999, pp. 2549-2554.

Mahmood et al., 3D-QSAR Comfa, Comsia Studies on Pyrazolo-Fused Azadecalins Derivatives as Selective Glucocorticoid Receptor Antagonists, Pharma Science Monitor, vol. 3, No. 3, Jul. 2012, pp. 2027-2055.

Nakawatase et al., Alzheimer's Disease and Related Dementia Cecil's Textbook of Medicine (Twenty-First Edition, vol. 1. W.B. Saunders Company, 2000, pp. 2042-2045.

Rehn et al., Antiinflammatory Action of Glucocorticoids—New Mechanisms for Old Drugs, The New England Journal of Medicine, vol. 353, No. 16, Oct. 20, 2005, pp. 1711-1723.

Sausville et al., Contributions of Human Tumor Xenografts to Anticancer Drug Development, Cancer Research, vol. 66, No. 7, Apr. 2006, pp. 3351-3354.

Schultz et al., Heteroatom Directed Photoarylation. Synthetic Potential of the Heteroatom Oxygen, Journal of the American Chemical Society, American Chemical Society, vol. 100, No. 7, Mar. 29, 1978, pp. 2150-2162.

Schultz et al., Studies Directed at a Synthesis of the Morphine Alkaloids. A Photochemical Approach, J. Org. Chem., American Chemical Society, vol. 50, No. 2, Jan. 1985, pp. 217-231.

Spitz et al., Mifepristone (RU 486)—A Modulator of Progestin and Glucocorticoid Action, The New England Journal of Medicine, Massachusetts Medical Society, vol. 329, No. 6, Aug. 5, 1993, pp. 404-412.

Uchida et al., An Efficient Access to the Optically Active Manzamine Tetracyclic Ring System, Tetrahedron Letters, vol. 40, Issue 1, Jan. 1, 1999, pp. 113-116.

European Patent Application No. EP14863514.7, Extended European Search Report dated May 4, 2017, 6 pages.

European Patent Application No. EP19177963.6, Extended European Search Report dated Jul. 25, 2019, 5 pages.

International Application No. PCT/US2005/008049, International Search Report and Written Opinion dated Jun. 15, 2005, 8 pages.

International Application No. PCT/US2010/034382, International Search Report and Written Opinion dated Jul. 9, 2010, 7 pages.

International Application No. PCT/US2011/049408, International Search Report and Written Opinion dated Jan. 30, 2012, 10 pages.

(56) References Cited

OTHER PUBLICATIONS

International Application No. PCT/US2013/027720, International Search Report and Written Opinion dated Jun. 17, 2013, 8 pages.
International Application No. PCT/US2014/066759, International Preliminary Report on Patentability dated Jun. 9, 2016, 6 pages.
International Application No. PCT/US2014/066759, International Search Report and Written Opinion dated Feb. 6, 2015, 9 pages.
U.S. Appl. No. 14/549,885, First Hunt Declaration dated Jan. 18, 2017, pp. 1-4.
U.S. Appl. No. 14/549,885, Second Hunt Declaration dated Jul. 7, 2017, 14 pages.

\* cited by examiner

THERAPEUTIC USES OF RELACORILANT, A HETEROARYL-KETONE FUSED AZADECALIN GLUCOCORTICOID RECEPTOR MODULATOR

CROSS-REFERENCE TO RELATED APPLICATIONS

This application claims, under 35 U.S.C. § 119(e), priority to and the benefit of U.S. Provisional Patent Application Ser. No. 62/809,327, filed Feb. 22, 2019; U.S. Provisional Patent Application Ser. No. 62/814,441, filed Mar. 6, 2019; and U.S. Provisional Patent Application Ser. No. 62/833,517, filed Apr. 12, 2019, the entire contents of all of which applications are hereby incorporated by reference in their entireties.

BACKGROUND

Cortisol is a glucocorticoid (GC) hormone that binds to a glucocorticoid receptor. Cortisol acts by binding to glucocorticoid receptor (GR) type II, also referred to as the cortisol receptor, an intracellular receptor which specifically binds to cortisol and/or cortisol analogs such as dexamethasone (See, e.g., Turner & Muller, J. Mol. Endocrinol. 35(2): 283-292 (2005)). The term GR includes isoforms of GR, recombinant GR and mutated GR. Another glucocorticoid receptor, the type I GR, also termed the "mineralocorticoid receptor (MR)" mediates the response to aldosterone.

Cortisol is produced in the adrenal glands; excess cortisol may be caused by adrenal abnormalities (e.g., an adrenal tumor). The excess cortisol may be caused by excess adrenocorticotrophic hormone (ACTH) release from the pituitary gland acting on the adrenal glands to produce the excess cortisol. Cortisol excess may be termed "hypercortisolemia" or "hypercortisolism". Patients suffering from hypercortisolemia often also exhibit excess blood glucose (hyperglycemia), may suffer from low potassium (hypokalemia), high blood pressure, cardiac disorders, or other disorders. Excess cortisol (which leads to excess activation of GR type II) characterizes and causes Cushing's syndrome, a debilitating chronic disease caused by high levels of cortisol, and characterized by high blood sugar, high blood pressure, disorders of the heart rhythm, weight gain (including a characteristic "hump" on the neck or back), hirsuteness, depression, and other symptoms.

When excess pituitary ACTH release causes the excess cortisol, the disorder is termed "Cushing's Disease". Such excess pituitary ACTH release is typically caused by a pituitary tumor. First-line treatment for Cushing's Disease involves surgery to remove the pituitary tumor; however, in many cases not all of the tumor is able to be resected (e.g., if the tumor has invaded cranial regions outside the *sella turcica*, or has invaded bone, or for other reasons), or it may grow back, or may have metastasized (more often for non-pituitary (ectopic) tumors than for pituitary tumors). In some cases, radiation treatment is applied following surgery. Conventional chemotherapy treatment often used for other tumors may be inapplicable for pituitary tumors, or may not be suitable for patients suffering from pituitary tumors. Medical treatment to reduce cortisol production, or to block the effects of cortisol (e.g., mifepristone (prescribed as)) KORLYM® is often administered, particularly when symptoms persist following surgery. Radiation and standard chemotherapy may have severe side-effects, which may make them unsuitable for Cushing's patients. Thus, medical (i.e., non-surgical) treatments for pituitary tumors which cause Cushing's Disease are needed, and improved treatments would be helpful.

Patients suffering from other disorders may also exhibit excess cortisol, and excess cortisol may be a cause of such disorders. For example, patients suffering from psychotic major depression typically exhibit excess cortisol. However, methods and compositions effective for reducing the effects of cortisol, and particularly for reducing the effects of excess cortisol, remain lacking.

SUMMARY

Disclosed herein are novel methods for treating a variety of disorders and diseases related to, or caused by, cortisol excess (hypercortisolemia or hypercortisolism), and for treating a variety of disorders and diseases which may be treated or symptoms ameliorated by reducing the effects or action of cortisol. Such diseases and disorders may include, without limitation, Cushing's syndrome, Cushing's Disease, hyperglycemia secondary to hypercortisolemia, liver diseases (e.g., fatty liver disease, non-alcoholic fatty liver disease (NAFLD), non-alcoholic steatohepatitis (NASH), alcoholic liver diseases, liver fibrosis, and other liver disorders), cardiac disorders (including, e.g., prolonged Q-T interval or other disorder of the heart rhythm), high blood pressure, hypercoagulopathy, cancers, bone disorders, blood clotting disorders, psychological disorders, weight gain (including weight gain due to antipsychotic medication), metabolic syndrome, pre-diabetes or diabetes, osteoporosis, hypogonadism, pseudoacromegaly, pituitary tumors, functional hypercortisolism, ACTH secreting tumors, peripheral neuropathy, dyslipidemia, and other diseases and disorders. Cortisol excess may also be found, for example, in patients with metabolic syndrome, pre-diabetes or diabetes; or may also be found, for example, in patients with liver disorders, such as, e.g., fatty liver disease, non-alcoholic fatty liver disease (NAFLD), non-alcoholic steatohepatitis (NASH), alcoholic liver diseases, liver fibrosis, and other liver disorders. The methods may include immunotherapy treatments. Reducing the effects of excess cortisol may improve the quality of life of a patient suffering from excess cortisol or its effects. Reducing the effects of excess cortisol may improve the psychological status of a patient suffering from excess cortisol or its effects.

The methods comprise administering to the subject an effective amount of a glucocorticoid receptor modulator (GRM) to reduce the effects of such cortisol excess, and, in embodiments, comprise administering to the subject an effective amount of a GRM along with another treatment (e.g., another pharmaceutical composition, or surgery, or radiation, or psychotherapy, or other treatment). In embodiments, the GRM is a nonsteroidal GRM. In embodiments, the GRM is a nonsteroidal selective GRM. In embodiments, the GRM is a nonsteroidal heteroaryl-ketone fused azadecalin selective GRM compound or a nonsteroidal octahydro fused azadecalin selective GRM compound. In preferred embodiments, the GRM is the nonsteroidal heteroaryl-ketone fused azadecalin selective GRM compound having the chemical name (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone, termed "relacorilant", having the formula

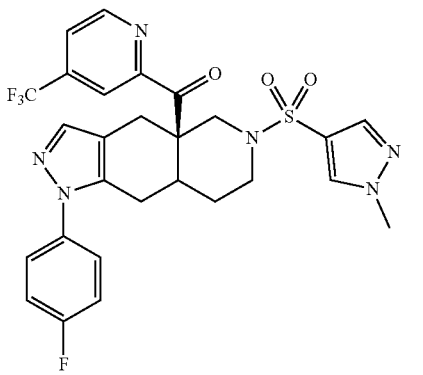

In embodiments, the methods disclosed herein include administration of a GRM, such as the heteroaryl-ketone fused azadecalin GRM relacorilant, to a patient in need of such treatment, to treat a disorder selected from Cushing's syndrome; Cushing's Disease; hyperglycemia secondary to hypercortisolemia; metabolic syndrome, pre-diabetes, or diabetes; a liver disease (e.g., fatty liver disease, non-alcoholic fatty liver disease (NAFLD), non-alcoholic steatohepatitis (NASH), alcoholic liver diseases, liver fibrosis, and other liver disorders); a cardiac disorder (including, e.g., prolonged Q-T interval or other disorder of the heart rhythm, with or without Left Ventricular Hypertrophy (LVH)); high blood pressure; cancer; a psychological disorder (e.g., depression, such as psychotic major depression); weight gain (including weight gain due to antipsychotic medication), and other diseases and disorders. A GRM, such as relacorilant, may be administered to a patient as a monotherapy; and, in embodiments, a GRM, such as relacorilant, may be administered to a patient along with another treatment. The GRM may be administered before, or after, or along with, or any combination thereof, another treatment. In addition, the methods disclosed herein include administration of a GRM, such as relacorilant, to a patient in need of diagnosis, to diagnose a disorder such as, e.g., Cushing's Disease.

In some cases, the GRM (e.g., relacorilant) is orally administered. In embodiments, the GRM is administered with food. In embodiments, the GRM is administered to a patient who is fasting. In some cases, the GRM (e.g., a relacorilant) is administered with at least one pharmaceutical agent. In some cases, the GRM (e.g., a relacorilant) is administered after the subject or patient has been administered at least one other pharmaceutical agent. In some cases, the GRM (e.g., a relacorilant) is administered before the subject or patient is administered at least one other pharmaceutical agent. In some cases, the GRM (e.g., a relacorilant) is administered to a subject after the subject or patient has undergone surgery. In some cases, the GRM (e.g., a relacorilant) is administered to a subject before the subject or patient undergoes surgery.

DETAILED DESCRIPTION

Introduction

Figure 1:
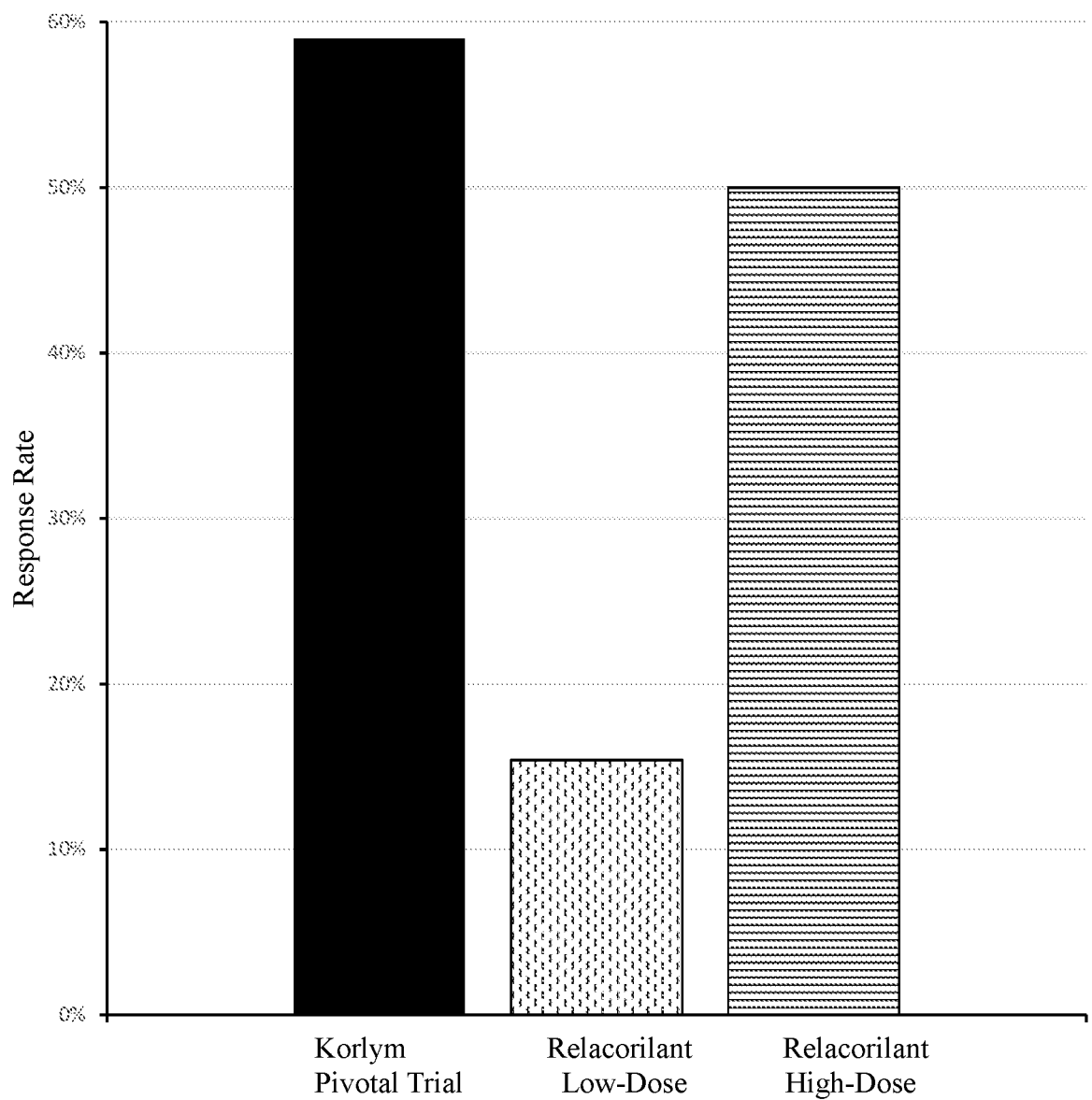
FIG. 1 Patients achieving clinically meaningful reductions in HbA1c, 2-hour oGTT or use of antidiabetic medications.

The methods disclosed herein can be used to treat a patient suffering from a disorder by administering an effective amount of a glucocorticoid receptor modulator (GRM), such as a selective glucocorticoid receptor modulator (SGRM), which in preferred embodiments is relacorilant (which may also be referred to as "RELA"). In embodiments, the methods disclosed herein include administration of a GRM, such as relacorilant, to a patient in need of such treatment, to treat a disorder selected from Cushing's syndrome; Cushing's Disease; hyperglycemia secondary to hypercortisolemia; metabolic syndrome, pre-diabetes, or diabetes; a liver disease (e.g., fatty liver disease, non-alcoholic fatty liver disease (NAFLD), non-alcoholic steatohepatitis (NASH), alcoholic liver diseases, liver fibrosis, and other liver disorders); a cardiac disorder (including, e.g., prolonged Q-T interval or other disorder of the heart rhythm, with or without Left Ventricular Hypertrophy (LVH)); high blood pressure; hypercoagulopathy; cancer; a psychological disorder (e.g., depression, such as psychotic major depression); weight gain (including weight gain due to antipsychotic medication); a bone disorder; a blood disorder, such as a blood clotting disorder; osteoporosis, hypogonadism, pseudoacromegaly, pituitary tumors, functional hypercortisolism, ACTH secreting tumors, peripheral neuropathy, dyslipidemia; and other diseases and disorders. A GRM or SGRM, such as relacorilant, may be administered with an immunotherapy agent, such as a checkpoint inhibitor, or other pharmaceutical agent. The methods disclosed herein can be used to treat a patient suffering from any disorder indicated by the results disclosed in Table 1. The methods disclosed herein can be used to normalize, in a patient, any diagnostic result indicated by the results disclosed in Table 1.

The methods disclosed herein comprising administering a GRM, such as relacorilant, can be used to diagnose a patient suspected of suffering from a disorder selected from Cushing's syndrome; Cushing's Disease; hyperglycemia secondary to hypercortisolemia; metabolic syndrome, pre-diabetes, or diabetes; a liver disease (e.g., fatty liver disease, non-alcoholic fatty liver disease (NAFLD), non-alcoholic steatohepatitis (NASH), alcoholic liver diseases, liver fibrosis, and other liver disorders); a cardiac disorder (including, e.g., prolonged Q-T interval or other disorder of the heart rhythm, with or without Left Ventricular Hypertrophy (LVH)); high blood pressure; hypercoagulopathy; cancer; a psychological disorder (e.g., depression, such as psychotic major depression); weight gain (including weight gain due to antipsychotic medication); a bone disorder; a blood clotting disorder; and other diseases and disorders. The methods disclosed herein comprising administering a GRM, such as relacorilant, can be used to improve the quality of life of a patient. The methods disclosed herein comprising administering a GRM, such as relacorilant, can be used to diagnose a patient suspected of suffering from any disorder indicated by the results disclosed in Table 1.

A GRM or SGRM, such as relacorilant, may be administered to a patient as a monotherapy; and, in embodiments, a GRM, such as relacorilant, may be administered to a patient along with another treatment. The GRM may be administered before, or after, or along with, or any combination thereof, another treatment. In addition, the methods disclosed herein include administration of a GRM, such as relacorilant, to a patient in need of diagnosis, to diagnose a disorder such as, e.g., Cushing's Disease.

In embodiments, the GRM is a nonsteroidal GRM.

In some cases, the GRM (e.g., a SGRM) is a nonsteroidal compound comprising a heteroaryl ketone fused azadecalin structure. In some cases, the heteroaryl ketone fused azadecalin compound has the formula:

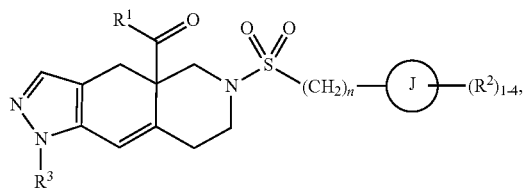

wherein $R^1$ is a heteroaryl ring having from 5 to 6 ring members and from 1 to 4 heteroatoms each independently selected from the group consisting of N, O and S, optionally substituted with 1-4 groups each independently selected from $R^{1a}$; each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, CN, N-oxide, $C_{3-8}$ cycloalkyl, and $C_{3-8}$ heterocycloalkyl; ring J is selected from the group consisting of a cycloalkyl ring, a heterocycloalkyl ring, an aryl ring and a heteroaryl ring, wherein the heterocycloalkyl and heteroaryl rings have from 5 to 6 ring members and from 1 to 4 heteroatoms each independently selected from the group consisting of N, O and S; each $R^2$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, CN, OH, $NR^{2a}R^{2b}$, $C(O)R^{2a}$, $C(O)OR^{2a}$, $C(O)NR^{2a}R^{2b}$, $SR^{2a}$, $S(O)R^{2a}$, $S(O)_2R^{2a}$, $C_{3-8}$ cycloalkyl, and $C_{3-8}$ heterocycloalkyl, wherein the heterocycloalkyl groups are optionally substituted with 1-4 $R^{2c}$ groups; alternatively, two $R^2$ groups linked to the same carbon are combined to form an oxo group (=O); alternatively, two $R^2$ groups are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2d}$ groups; $R^{2a}$ and $R^{2b}$ are each independently selected from the group consisting of hydrogen and $C_{1-6}$ alkyl; each $R^{2c}$ is independently selected from the group consisting of hydrogen, halogen, hydroxy, $C_{1-6}$ alkoxy, $C_{1-6}$ haloalkoxy, CN, and $NR^{2a}R^{2b}$; each $R^{2d}$ is independently selected from the group consisting of hydrogen and $C_{1-6}$ alkyl, or two $R^{2d}$ groups attached to the same ring atom are combined to form (=O); $R^3$ is selected from the group consisting of phenyl and pyridyl, each optionally substituted with 1-4 $R^{3a}$ groups; each $R^{3a}$ is independently selected from the group consisting of hydrogen, halogen, and $C_{1-6}$ haloalkyl; and subscript n is an integer from 0 to 3;

or salts and isomers thereof. Such compounds, including relacorilant, are disclosed, for example, in U.S. Pat. No. 8,559,784, the entire contents of which is hereby incorporated by reference in its entirety. Uses and discussion regarding such compounds are further disclosed, for example, in U.S. Pat. Nos. 9,273,047; 9,943,505; 9,707,223; 9,956,216; 10,117,852; and 10,151,763, the entire contents of which patents are each hereby incorporated by reference in their entireties.

In preferred embodiments, the GRM is the nonsteroidal heteroaryl-ketone fused azadecalin GRM compound having the chemical name (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone, termed "relacorilant", having the formula

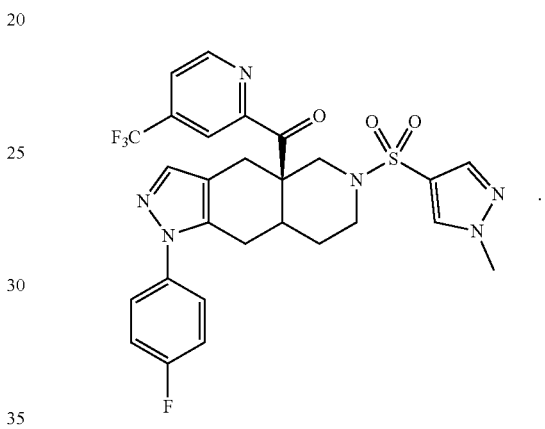

In embodiments, the GRM is the nonsteroidal heteroaryl-ketone fused azadecalin GRM compound is the compound having the chemical name (R)-(1-(4-flurophenyl)-6-((4-(trifluoromethyl)phenyl)sulfonyl)-4,4a,5,6,7,8-hexahydro-1H-pyrazolo[3,4-g]isoquinolin-4a-yl)(thiazol-2-yl)methanone, termed "CORT122928", having the formula

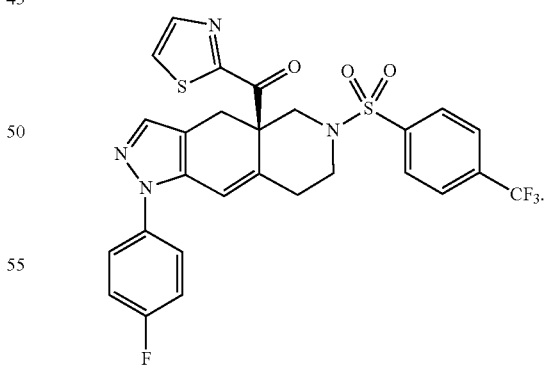

In embodiments, the GRM is the nonsteroidal heteroaryl-ketone fused azadecalin GRM compound having the chemical name (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(pyridin-2-yl)methanone, termed "CORT113176", having the formula

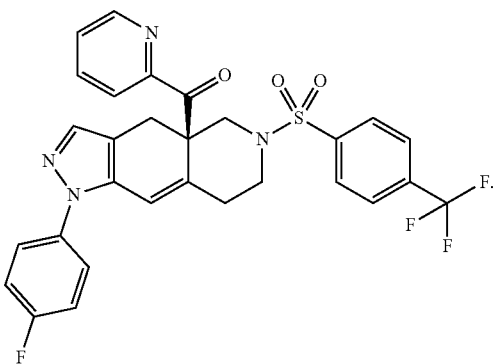 [SMILES: O=C(c1ccccn1)[C@]12Cc3cnn(-c4ccc(F)cc4)c3C=C1CCN(S(=O)(=O)c1ccc(C(F)(F)F)cc1)C2]

In some cases, the GRM (e.g., a SGRM) is a nonsteroidal compound comprising an octahydro fused azadecalin structure. Exemplary GRMs comprising an octahydro fused azadecalin structure include those described in U.S. Pat. No. 10,047,082 and can be prepared as described therein, the disclosure of which U.S. patent is incorporated herein in its entirety. Such exemplary GRMs may be SGRMs. In some cases, the octahydro fused azadecalin compound has the formula:

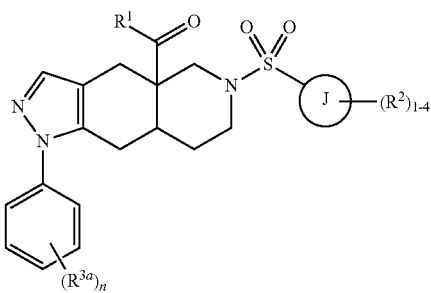

wherein
R$^1$ is a heteroaryl ring having from 5 to 6 ring members and from 1 to 4 heteroatoms each independently selected from the group consisting of N, O and S, optionally substituted with 1-4 groups each independently selected from R$^{1a}$;
each R$^{1a}$ is independently selected from the group consisting of hydrogen, C$_{1-6}$ alkyl, halogen, C$_{1-6}$ haloalkyl, C$_{1-6}$ alkoxy, C$_{1-6}$ haloalkoxy, N-oxide, and C$_{3-8}$ cycloalkyl;
ring J is selected from the group consisting of an aryl ring and a heteroaryl ring having from 5 to 6 ring members and from 1 to 4 heteroatoms each independently selected from the group consisting of N, O and S;
each R$^2$ is independently selected from the group consisting of hydrogen, C$_{1-6}$ alkyl, halogen, C$_{1-6}$ haloalkyl, C$_{1-6}$ alkoxy, C$_{1-6}$ haloalkoxy, C$_{1-6}$ alkyl-C$_{1-6}$ alkoxy, —CN, —OH, —NR$^{2a}$R$^{2b}$, —C(O)R$^{2a}$, —C(O)OR$^{2a}$, —C(O)NR$^{2a}$R$^{2b}$, —SR$^{2a}$, —S(O)R$^{2a}$, —S(O)$_2$R$^{2a}$, C$_{3-8}$ cycloalkyl, and C$_{3-8}$ heterocycloalkyl having from 1 to 3 heteroatoms each independently selected from the group consisting of N, O and S;
alternatively, two R$^2$ groups on adjacent ring atoms are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 R$^{2'}$ groups;
R$^{2a}$, R$^{2b}$ and R$^{2c}$ are each independently selected from the group consisting of hydrogen and C$_{1-6}$ alkyl;
each R$^{3a}$ is independently halogen; and
subscript n is an integer from 0 to 3;
or salts and isomers thereof.

In embodiments, the octahydro fused azadecalin compound has the formula:

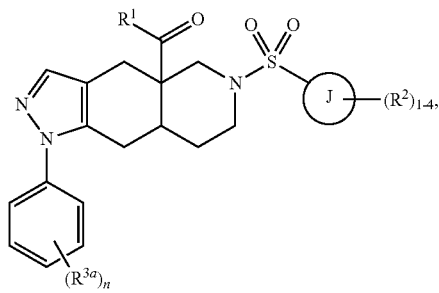

wherein R$^1$ is selected from the group consisting of pyridine and thiazole, optionally substituted with 1-4 groups each independently selected from R$^{1a}$; each R$^{1a}$ is independently selected from the group consisting of hydrogen, C$_{1-6}$ alkyl, halogen, C$_{1-6}$ haloalkyl, C$_{1-6}$ alkoxy, C$_{1-6}$ haloalkoxy, N-oxide, and C$_{3-8}$ cycloalkyl; ring J is selected from the group consisting of phenyl, pyridine, pyrazole, and triazole; each IV is independently selected from the group consisting of hydrogen, C$_{1-6}$ alkyl, halogen, C$_{1-6}$ haloalkyl, and —CN; R$^{3a}$ is F; subscript n is an integer from 0 to 3; or salts and isomers thereof.

In embodiments, the GRM is the nonsteroidal octahydro fused azadecalin GRM compound having the chemical name ((4aR,8aS)-1-(4-fluorophenyl)-6-((2-methyl-2H-1,2,3-triazol-4-yl)sulfonyl)-4,4a,5,6,7,8,8a,9-octahydro-1H-pyrazolo[3,4-g]isoquinolin-4a-yl)(4-(trifluoromethyl)pyridin-2-yl)methanone, termed "CORT125281", having the formula

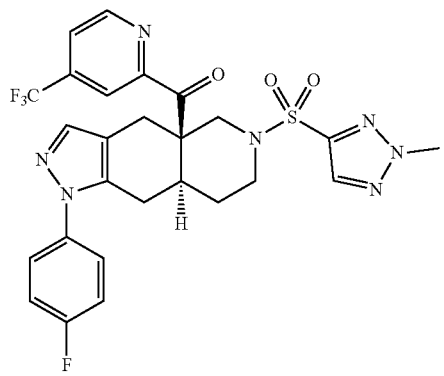 [SMILES: Cn1ncc(S(=O)(=O)N2CC[C@H]3Cc4c(cnn4-c4ccc(F)cc4)C[C@]3(C(=O)c3cc(C(F)(F)F)ccn3)C2)n1]

In embodiments, the GRM is the nonsteroidal octahydro fused azadecalin GRM compound having the chemical name ((4aR,8aS)-1-(4-fluorophenyl)-6-((2-isopropyl-2H-1,2,3-triazol-4-yl)sulfonyl)-4,4a,5,6,7,8,8a,9-octahydro-1H-pyrazolo[3,4-g]isoquinolin-4a-yl)(thiazol-2-yl)methanone, termed "CORT125329", having the formula:

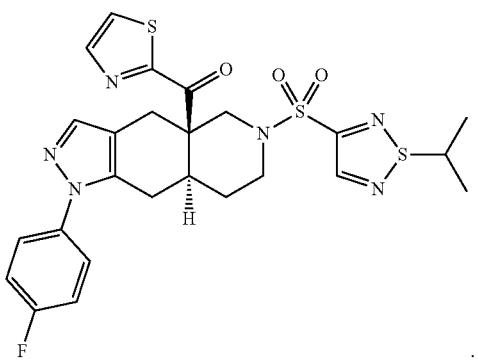

Definitions

As used herein, the term "subject" or "patient" refers to a human or non-human organism. Thus, the methods and compositions described herein are applicable to both human and veterinary disease. In certain embodiments, subjects are "patients," i.e., living humans that are receiving medical care for a disease or condition. This includes persons with no defined illness who are being investigated for signs of pathology. Preferred are subjects who have an existing diagnosis of a Cushing's syndrome, an example of a disease which may be treated by the compositions and methods of the present invention.

A disease, disorder, abnormality, adverse event, or condition causing discomfort, distress, or disease may be termed a "morbidity". A morbidity associated with a disease or disorder, such as, e.g., hypercortisolemia, Cushing's syndrome, Cushing's disease, etc., may be termed a "comorbidity".

Acronyms used herein include:
ACTH adrenocorticotropic hormone
proACTH pro-protein of ACTH
POMC pro-opiomelanocortin
aPTT activated partial thromboplastin time
ALT alanine aminotransferase (or "serum glutamic-pyruvic transaminase" (SGPT))
AST aspartate aminotransferase (or "serum glutamic-oxaloacetic transaminase" (SGOT))
AUC area under the concentration-time curve
$AUC_{0-24\ h}$ area under the concentration-time curve over 24 hours
$AUC_{glucose}$ area under the concentration-time curve for glucose
$AUC_{insulin}$ area under the concentration-time curve for glucose
BDI Beck Depression Inventory is a 21-question self-report inventory that measures depression. BDI-II Total Score is the total score of Beck Depression Inventory II Cushing QOL Score Cushing Quality of Life Score. A patient questionnaire that evaluates the health-related quality of life in patients with Cushing's syndrome
ECG electrocardiogram
HOMA-IR Homeostatic model assessment (HOMA) insulin resistance (IR)
IR insulin resistance
HbA1c glycated hemoglobin
IGT impaired glucose tolerance (may be diagnosed with oGTT)
mITT modified intention to treat
mPP modified protocol population
NTx N-telopeptides of type 1 collagen
oGTT oral glucose tolerance test
PR interval time between onset of P wave and the R (peak of the QRS complex)
QRS Duration time between onset of Q wave and return to baseline of the S wave
QT Interval time between onset of the QRS complex and time the T wave returns to baseline
QTcB Interval corrected QT interval (Bazett's correction)
RR Interval time between two R waves (peaks of the QRS complex)
UFC urinary free cortisol
Urinary NTx Urinary N-telopeptides cross-links As used herein, the term "Adrenocorticotrophic Hormone" (ACTH) refers to the peptide hormone produced by the anterior pituitary gland that stimulates the adrenal cortex to secrete glucocorticoid hormones, which help cells synthesize glucose, catabolize proteins, mobilize free fatty acids and inhibit inflammation in allergic responses. One such glucocorticoid hormone is cortisol, which regulates metabolism of carbohydrate, fat, and protein metabolism.

As used herein, the term "effective amount" or "therapeutic amount" refers to an amount of a pharmacological agent effective to treat, eliminate, or mitigate at least one symptom of the disease being treated. In some cases, "therapeutically effective amount" or "effective amount" can refer to an amount of a functional agent or of a pharmaceutical composition useful for exhibiting a detectable therapeutic or inhibitory effect. The effect can be detected by any assay method known in the art. The effective amount can be an amount effective to reduce symptoms of cortisol excess, or of hyperglycemia, or of high blood pressure, or of liver fat or fibrosis, or of depression, or bring about other desired beneficial clinical outcomes related to patient improvement.

As used herein, the terms "administer," "administering," "administered" or "administration" refer to providing a compound or a composition (e.g., one described herein), to a subject or patient.

As used herein, the term "fasting" refers to a subject or patient who has not eaten for at least one hour, or at least two hours, or at least three hours, or at least four hours, or more. In preferred embodiments, a fasting subject or patient has not eaten for at least four hours. When a pharmaceutical composition is administered to a fasting subject or patient, the pharmaceutical composition is administered without food, and the subject or patient does not eat for at least an hour after drug administration.

As used herein, the terms "hypercortisolemia" and "hypercortisolism" are interchangeable and refer to excess cortisol. A patient suffering from hypercortisolemia has Cushing's syndrome, and may suffer from symptoms and other disorders caused by, or related to, such cortisol excess.

As used herein, the term "Cushing's syndrome" refers to disorders caused by excessive activity of the stress hormone cortisol. Endogenous Cushing's syndrome is an orphan disease that most often affects adults aged 20-50. In many cases the disease is caused by a pituitary tumor, or an adrenal tumor. Symptoms vary, but most people experience one or more of the following manifestations: high blood sugar, metabolic syndrome, pre-diabetes, or diabetes, high blood pressure, upper-body obesity, rounded face, increased fat around the neck, thinning arms and legs, severe fatigue and weak muscles. Irritability, anxiety, cognitive disturbances and depression are also common. Cushing's syndrome can affect every organ system in the body and can be lethal if not treated effectively.

As used herein, the term "metabolic syndrome" refers to a syndrome characterized by high blood glucose, high blood pressure, excess body fat (particularly around the waist), high levels of blood lipids, and other factors. Metabolic syndrome may indicate increased risk of cardiovascular disease, diabetes, liver diseases, and other diseases.

As used herein, the term "pre-diabetes" refers to a condition in which a subject may have one or more of elevated blood glucose, abnormal glucose tolerance test results, and other symptoms such as, e.g., elevated blood pressure, excess weight, excess blood lipids, where such excesses or abnormalities may be slight.

As used herein, the term "diabetes" refers to the disorder of blood glucose typified by high blood glucose levels, impaired insulin response, presence or high levels of ketones in the urine, and other symptoms as known in the clinical arts. Patients often experience thirst, frequent urination, fatigue, irritability, and other symptoms.

As used herein, the term "immunotherapy" refers to disease treatments, typically cancer treatments, that affect the immune system of the patient (e.g., by activating or suppressing its action). Some immunotherapies include administration of "checkpoint inhibitors" which enhance the action of immune system T cells to attack cancer cells. Some immunotherapies include use of the patients T cells which have been exposed to cancer cells or cancer markers, to enhance the treatment of cancer in the patent.

As used herein, the term "checkpoint inhibitor" refers to a drug, which may be, e.g., a small molecule drug or may be an antibody, which inhibits the action of proteins or other aspects of immune system cells which reduce or block the ability of T cells to attack cancer cells. The targets of checkpoint inhibitors may be found in or on T cells, or may be found in or on cancer cells. Targets of checkpoint inhibitors include the proteins PD-1, PDL-1, B7-1, B7-2 and others. Checkpoint inhibitors include antibodies to PD-1, PDL-1, CTLA-4, B7-1, B7-2 and others. For example, the antibody drugs Pembrolizumab (Keytruda), Nivolumab (Opdivo), and Cemiplimab (Libtayo) inhibit PD-1, and the antibody drugs Atezolizumab (Tecentriq), Avelumab (Bavencio), and Durvalumab (Imfinzi) inhibit PDL-1.

As used herein, the term "combination therapy" refers to the administration of at least two pharmaceutical agents to a subject to treat a disease. The two agents may be administered simultaneously, or sequentially in any order during the entire or portions of the treatment period. The at least two agents may be administered following the same or different dosing regimens. In some cases, one agent is administered following a scheduled regimen while the other agent is administered intermittently. In some cases, both agents are administered intermittently. In some embodiments, the one pharmaceutical agent, e.g., a SGRM, is administered daily, and the other pharmaceutical agent, e.g., a pharmaceutical agent, is administered every two, three, or four days.

As used herein, the term "compound" is used to denote a molecular moiety of unique, identifiable chemical structure. A molecular moiety ("compound") may exist in a free species form, in which it is not associated with other molecules. A compound may also exist as part of a larger aggregate, in which it is associated with other molecule(s), but nevertheless retains its chemical identity. A solvate, in which the molecular moiety of defined chemical structure ("compound") is associated with a molecule(s) of a solvent, is an example of such an associated form. A hydrate is a solvate in which the associated solvent is water. The recitation of a "compound" refers to the molecular moiety itself (of the recited structure), regardless of whether it exists in a free form or an associated form.

As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The terms "glucocorticoid" ("GC") or "glucocorticosteroid" equally refer to a steroid hormone that binds to a glucocorticoid receptor. GCs are typically characterized by having 21 carbon atoms, an $\alpha,\beta$-unsaturated ketone in ring A, and an $\alpha$-ketol group attached to ring D. They differ in the extent of oxygenation or hydroxylation at C-11, C-17, and C-19; see Rawn, "Biosynthesis and Transport of Membrane Lipids and Formation of Cholesterol Derivatives," in Biochemistry, Daisy et al. (eds.), 1989, pg. 567.

A mineralocorticoid receptor (MR), also known as a type I glucocorticoid receptor (GR I), is activated by aldosterone in humans.

As used herein, the term "Glucocorticoid receptor" ("GR") refers to a family of intracellular receptors which specifically bind to cortisol and/or cortisol analogs. The glucocorticoid receptor is also referred to as the cortisol receptor. The term includes isoforms of GR, recombinant GR and mutated GR. "Glucocorticoid receptor" ("GR") refers to the type II GR which specifically binds to cortisol and/or cortisol analogs such as dexamethasone (See, e.g., Turner & Muller, J. Mol. Endocrinol. Oct. 1, 2005 35 283-292).

"Glucocorticoid receptor modulator" (GRM) refers to any compound which modulates any biological response associated with the binding of GR to an agonist. For example, a GR agonist, such as dexamethasone, increases the activity of tyrosine aminotransferase (TAT) in HepG2 cells (a human liver hepatocellular carcinoma cell line; ECACC, UK). Accordingly, GR modulators of the present invention can be identified by measuring the ability of the compound to modulate the effect of dexamethasone. TAT activity can be measured as outlined in the literature by A. Ali et al., J. Med. Chem., 2004, 47, 2441-2452. A modulator is a compound with an $EC_{50}$ (half maximal effective concentration) of less than 10 micromolar. See Example 1, infra.

As used herein, the term "selective glucocorticoid receptor modulator" (SGRM) refers to any composition or compound which modulates any biological response associated with the binding of a GR to an agonist. By "selective," the drug preferentially binds to the GR rather than other nuclear receptors, such as the progesterone receptor (PR), the mineralocorticoid receptor (MR) or the androgen receptor (AR). It is preferred that the selective glucocorticoid receptor modulator bind GR with an affinity that is 10× greater ($1/10^{th}$ the $K_d$ value) than its affinity to the MR, AR, or PR, both the MR and PR, both the MR and AR, both the AR and PR, or to the MR, AR, and PR. In a more preferred embodiment, the selective glucocorticoid receptor modulator binds GR with an affinity that is 100× greater ($1/100^{th}$ the $K_d$ value) than its affinity to the MR, AR, or PR, both the MR and PR, both the MR and AR, both the AR and PR, or to the MR, AR, and PR. In another embodiment, the selective glucocorticoid receptor modulator binds GR with an affinity that is 1000× greater ($1/1000^{th}$ the $K_d$ value) than its affinity to the MR, AR, or PR, both the MR and PR, both the MR and AR, both the AR and PR, or to the MR, AR, and PR.

As used herein, the terms "selective glucocorticoid receptor modulator" and "SGRM" do not include ORG 34517, or 11-(substituted phenyl)-estra-4,9-diene derivatives, or 11-(substituted phenyl)-estra-4,9-diene derivatives of the following formula:

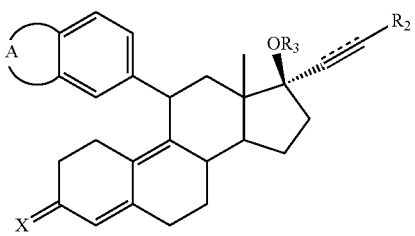

(I)

wherein A is a residue of a 5- or 6-membered ring containing 2 heteroatoms which are not connected to each other and independently selected from O and S, the ring being optionally substituted with one or more halogen atoms, or A is a residue of a 5- or 6-membered ring wherein no double C—C bonds are present, containing 1 heteroatom selected from O and S, which heteroatom is connected to the phenyl group at the position indicated with an asterisk, the ring being optionally substituted with one or more halogen atoms; R1 is H or 1-oxo(1-4C)alkyl; R2 is H, (1-8C)alkyl, halogen or CF3; X is selected from (H, OH), O, and NOH; and the interrupted line represents an optional bond (see, e.g., claim 1 of U.S. Pat. No. 8,658,128).

As used herein, the term "composition" is intended to encompass a product comprising the specified ingredients such as the said compounds, their tautomeric forms, their derivatives, their analogues, their stereoisomers, their polymorphs, their deuterated species, their pharmaceutically acceptable salts, esters, ethers, metabolites, mixtures of isomers, their pharmaceutically acceptable solvates and pharmaceutically acceptable compositions in specified amounts, as well as any product which results, directly or indirectly, from combination of the specified ingredients in the specified amounts. Such term in relation to a pharmaceutical composition is intended to encompass a product comprising the active ingredient (s), and the inert ingredient (s) that make up the carrier, as well as any product which results, directly or indirectly, in combination, complexation or aggregation of any two or more of the ingredients, or from dissociation of one or more of the ingredients, or from other types of reactions or interactions of one or more of the ingredients. Accordingly, the pharmaceutical compositions of the present invention are meant to encompass any composition made by admixing compounds of the present invention and their pharmaceutically acceptable carriers.

In some embodiments, the term "consisting essentially of" refers to a composition in a formulation whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" can refer to compositions which contain the active ingredient and components which facilitate the release of the active ingredient. For example, the composition can contain one or more components that provide extended release of the active ingredient over time to the subject. In some embodiments, the term "consisting" refers to a composition, which contains the active ingredient and a pharmaceutically acceptable carrier or excipient.

"Pharmaceutically-acceptable excipient" and "pharmaceutically-acceptable carrier" refer to a substance that aids the administration of an active agent to—and absorption by—a subject and can be included in the compositions of the present invention without causing a significant adverse toxicological effect on the patient. Non-limiting examples of pharmaceutically-acceptable excipients include water, NaCl, normal saline solutions, lactated Ringer's, normal sucrose, normal glucose, binders, fillers, disintegrants, lubricants, coatings, sweeteners, flavors and colors, and the like. One of ordinary skill in the art will recognize that other pharmaceutical excipients are useful in the present invention.

As used herein, the phrase "nonsteroidal backbone" in the context of SGRMs refers to SGRMs that do not share structural homology to, or are not modifications of, cortisol with its steroid backbone containing seventeen carbon atoms, bonded in four fused rings. Such compounds include synthetic mimetics and analogs of proteins, including partially peptidic, pseudopeptidic and non-peptidic molecular entities.

Nonsteroidal SGRM compounds include SGRMs comprising a fused azadecalin structure (which may also be termed a fused azadecalin backbone), SGRMs comprising a heteroaryl ketone fused azadecalin structure (which may also be termed a heteroaryl ketone fused azadecalin backbone), and SGRMs comprising an octahydro fused azadecalin structure (which may also be termed an octahydro fused azadecalin backbone). Exemplary nonsteroidal glucocorticoid receptor modulators comprising a fused azadecalin structure include those described in U.S. Pat. Nos. 7,928,237 and 8,461,172. Exemplary nonsteroidal glucocorticoid receptor modulators comprising a heteroaryl ketone fused azadecalin structure include those described in U.S. Pat. No. 8,859,774 and continuations thereof. Exemplary nonsteroidal glucocorticoid receptor modulators comprising an octahydro fused azadecalin structure include those described in U.S. Pat. No. 10,047,082. The entire contents of all patents and patent applications cited herein are hereby incorporated by reference in their entireties.

Where substituent groups are specified by their conventional chemical formulae, written from left to right, they equally encompass the chemically identical substituents that would result from writing the structure from right to left, e.g., —CH$_2$O— is equivalent to —OCH$_2$—.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$, and $C_{5-6}$. For example, $C_{1-6}$ alkyl includes, but is not limited to, methyl, ethyl, propyl, isopropyl, butyl, isobutyl, sec_butyl, tert_butyl, pentyl, isopentyl, and hexyl.

"Alkoxy" refers to an alkyl group having an oxygen atom that connects the alkyl group to the point of attachment: alkyl-O—. As for the alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc.

"Halogen" refers to fluorine, chlorine, bromine, and iodine.

"Haloalkyl" refers to alkyl, as defined above, where some or all of the hydrogen atoms are replaced with halogen atoms. As for the alkyl group, haloalkyl groups can have any suitable number of carbon atoms, such as $C_{1-6}$, and include trifluoromethyl, fluoromethyl, etc.

The term "perfluoro" can be used to define a compound or radical where all the hydrogens are replaced with fluorine. For example, perfluoromethane includes 1,1,1-trifluoromethyl.

"Haloalkoxy" refers to an alkoxy group where some or all of the hydrogen atoms are substituted with halogen atoms. As for the alkyl group, haloalkoxy groups can have any suitable number of carbon atoms, such as $C_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2,-trifluoroethoxy, and perfluoroethoxy.

"Cycloalkyl" refers to a saturated or partially unsaturated, monocyclic, fused bicyclic, or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2]bicyclooctane, decahydronaphthalene, and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to, cyclopropyl, cyclobutyl, cyclopentyl, cyclohexyl, cycloheptyl, and cyclooctyl. When cycloalkyl is a saturated monocyclic $C_{3-6}$ cycloalkyl, exemplary groups include, but are not limited to, cyclopropyl, cyclobutyl, cyclopentyl, and cyclohexyl.

"Heterocycloalkyl" refers to a saturated ring system having from 3 to 12 ring members and from 1 to 4 heteroatoms of N, O, and S. Additional heteroatoms can also be useful, including but not limited to, B, Al, Si, and P. The heteroatoms can also be oxidized, such as, but not limited to, —S(O)— and —S(O)$_2$—. Heterocycloalkyl groups can include any number of ring atoms, such as 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxalidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxazolidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

"Aryl" refers to an aromatic ring system having any suitable number of ring atoms and any suitable number of rings. Aryl groups can include any suitable number of ring atoms, such as 6, 7, 8, 9, 10, 11, 12, 13, 14, 15, or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, that has a methylene linking group. Some aryl groups have from 6 to 12 ring members, such as phenyl, naphthyl, or biphenyl. Other aryl groups have from 6 to 10 ring members, such as phenyl or naphthyl. Some other aryl groups have 6 ring members, such as phenyl. Aryl groups can be substituted or unsubstituted.

"Heteroaryl" refers to a monocyclic, fused bicyclic, or tricyclic aromatic ring assembly containing 5 to 16 ring atoms, where from 1 to 5 of the ring atoms are a heteroatom such as N, O, or S. Additional heteroatoms can also be useful, including but not limited to, B, Al, Si, and P. The heteroatoms can also be oxidized, such as, but not limited to, N-oxide, —S(O)—, and —S(O)$_2$—. Heteroaryl groups can include any number of ring atoms, such as 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5; or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4-, and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

The heteroaryl groups can be linked via any position on the ring. For example, pyrrole includes 1-, 2-, and 3-pyrrole; pyridine includes 2-, 3- and 4-pyridine; imidazole includes 1-, 2-, 4- and 5-imidazole; pyrazole includes 1-, 3-, 4- and 5-pyrazole; triazole includes 1-, 4- and 5-triazole; tetrazole includes 1- and 5-tetrazole; pyrimidine includes 2-, 4-, 5- and 6-pyrimidine; pyridazine includes 3- and 4-pyridazine; 1,2,3-triazine includes 4- and 5-triazine; 1,2,4-triazine includes 3-, 5- and 6-triazine; 1,3,5-triazine includes 2-triazine; thiophene includes 2- and 3-thiophene; furan includes 2- and 3-furan; thiazole includes 2-, 4- and 5-thiazole; isothiazole includes 3-, 4- and 5-isothiazole; oxazole includes 2-, 4- and 5-oxazole; isoxazole includes 3-, 4- and 5-isoxazole; indole includes 1-, 2- and 3-indole; isoindole includes 1- and 2-isoindole; quinoline includes 2-, 3- and 4-quinoline; isoquinoline includes 1-, 3- and 4-isoquinoline; quinazoline includes 2- and 4-quinoazoline; cinnoline includes 3- and 4-cinnoline; benzothiophene includes 2- and 3-benzothiophene; and benzofuran includes 2- and 3-benzofuran.

Some heteroaryl groups include those having from 5 to 10 ring members and from 1 to 3 ring atoms including N, O, or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring heteroatoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

"Heteroatoms" refers to O, S, or N.

"Salt" refers to acid or base salts of the compounds used in the methods of the present invention. Illustrative examples of pharmaceutically-acceptable salts are mineral acid (hydrochloric acid, hydrobromic acid, phosphoric acid, and the like) salts, organic acid (acetic acid, propionic acid, glutamic acid, citric acid, and the like) salts, and quaternary ammonium (methyl iodide, ethyl iodide, and the like) salts. It is understood that the pharmaceutically-acceptable salts are non-toxic. Additional information on suitable pharmaceutically-acceptable salts can be found in Remington's Pharmaceutical Sciences, 17th ed., Mack Publishing Company, Easton, Pa., 1985, which is incorporated herein by reference.

"Isomers" refers to compounds with the same chemical formula but which are structurally distinguishable.

"Tautomer" refers to one of two or more structural isomers which exist in equilibrium and which are readily converted from one form to another.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to produce compounds which are not inherently unstable—and/or would be known to one of ordinary skill in the art as likely to be unstable under ambient conditions—such as aqueous, neutral, or physiological conditions.

The methods disclosed herein are applicable for treating patients suffering from Cushing's syndrome, Cushing's Disease, and other disorders caused by, or characterized by, or including as a symptom, cortisol excess (hypercortisolemia); hyperglycemia secondary to hypercortisolemia; metabolic syndrome, pre-diabetes, or diabetes; a liver disease (e.g., fatty liver disease, non-alcoholic fatty liver disease (NAFLD), non-alcoholic steatohepatitis (NASH), alcoholic liver diseases, liver fibrosis, and other liver disorders); a cardiac disorder (including, e.g., prolonged Q-T interval or other disorder of the heart rhythm, with or without Left Ventricular Hypertrophy (LVH)); high blood pressure; cancer; a psychological disorder (e.g., depression, such as psychotic major depression); weight gain (including weight gain due to antipsychotic medication), and other diseases and disorders.

Generally, treatment of cortisol excess (hypercortisolemia) can be provided by administering an effective amount of a pharmaceutical agent in combination with an effective amount of a glucocorticoid receptor modulator (GRM) of any chemical structure or mechanism of action. In embodiments, the GRM is a selective GRM (SGRM). In embodiments, treatment of cortisol excess can be provided by administering an effective amount of a pharmaceutical agent in combination with an effective amount of a SGRM. In preferred embodiments, treatment of cortisol excess can be provided by administering an effective amount of a pharmaceutical agent in combination with an effective amount of a nonsteroidal SGRM. Provided herein are classes of exemplary GRMs, and in particular, exemplary nonsteroidal SGRMs, and specific members of such classes. However, one of skill in the art will readily recognize other related or unrelated GRMs and SGRMs that can be employed in the treatment methods described herein.

Exemplary GRMs comprising a heteroaryl ketone fused azadecalin structure include those described in U.S. Pat. No. 8,859,774, which can be prepared as disclosed therein, and is incorporated herein in its entirety. Such exemplary GRMs may be SGRMs. In some cases, the GRM comprising a heteroaryl ketone fused azadecalin structure has the following structure:

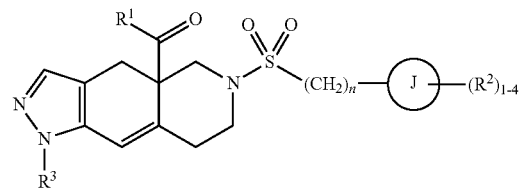

wherein
$R^1$ is a heteroaryl ring having from 5 to 6 ring members and from 1 to 4 heteroatoms each independently selected from the group consisting of N, O and S, optionally substituted with 1-4 groups each independently selected from $R^{1a}$;
each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, —CN, N-oxide, $C_{3-8}$ cycloalkyl, and $C_{3-8}$ heterocycloalkyl;

ring J is selected from the group consisting of a cycloalkyl ring, a heterocycloalkyl ring, an aryl ring and a heteroaryl ring, wherein the heterocycloalkyl and heteroaryl rings have from 5 to 6 ring members and from 1 to 4 heteroatoms each independently selected from the group consisting of N, O and S;

each $R^2$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, —CN, —OH, —$NR^{2a}R^{2b}$, —$C(O)R^{2a}$, —$C(O)OR^{2a}$, —$C(O)NR^{2a}R^{2b}$, —$SR^{2a}$, —$S(O)R^{2a}$, —$S(O)_2R^{2a}$, $C_{3-8}$ cycloalkyl, and $C_{3-8}$ heterocycloalkyl, wherein the heterocycloalkyl groups are optionally substituted with 1-4 $R^2C$ groups;

alternatively, two $R^2$ groups linked to the same carbon are combined to form an oxo group (=O);

alternatively, two $R^2$ groups are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2d}$ groups;

$R^{2a}$ and $R^{2b}$ are each independently selected from the group consisting of hydrogen and $C_{1-6}$ alkyl;

each $R^{2c}$ is independently selected from the group consisting of hydrogen, halogen, hydroxy, $C_{1-6}$ alkoxy, $C_{1-6}$ haloalkoxy, —CN, and —$NR^{2a}R^{2b}$;

each $R^{2d}$ is independently selected from the group consisting of hydrogen and $C_{1-6}$ alkyl, or two $R^{2d}$ groups attached to the same ring atom are combined to form (=O);

$R^{3a}$ is selected from the group consisting of phenyl and pyridyl, each optionally substituted with 1-4 $R^{3a}$ groups;

each $R^{3a}$ is independently selected from the group consisting of hydrogen, halogen, and $C_{1-6}$ haloalkyl; and subscript n is an integer from 0 to 3;

or salts and isomers thereof.

In preferred embodiments, the GRM is the nonsteroidal heteroaryl-ketone fused azadecalin GRM compound having the chemical name (R)-(1-(4-fluorophenyl)-6-(1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone, termed "relacorilant", having the formula

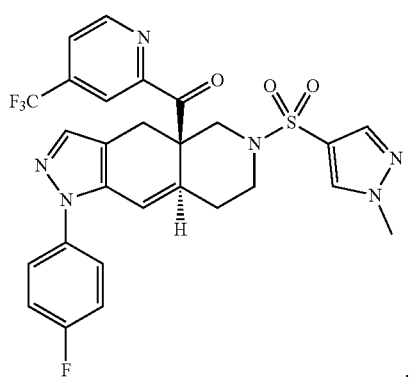

Exemplary GRMs comprising an octahydro fused azadecalin structure include those described in U.S. Pat. No. 10,047,082 and can be prepared as described therein, the disclosure of which U.S. patent is incorporated herein in its entirety. Such exemplary GRMs may be SGRMs. In some cases, the GRM comprising an octahydro fused azadecalin structure has the following structure:

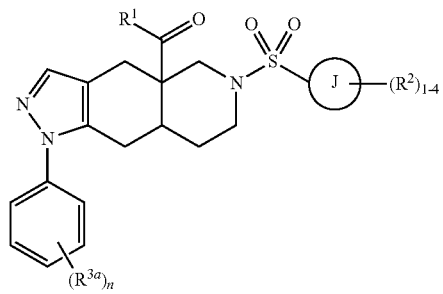

wherein $R^1$ is a heteroaryl ring having from 5 to 6 ring members and from 1 to 4 heteroatoms each independently selected from the group consisting of N, O and S, optionally substituted with 1-4 groups each independently selected from $R^{1a}$;

each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, N-oxide, and $C_{3-8}$ cycloalkyl;

ring J is selected from the group consisting of an aryl ring and a heteroaryl ring having from 5 to 6 ring members and from 1 to 4 heteroatoms each independently selected from the group consisting of N, O and S;

each $R^2$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, —CN, —OH, —$NR^{2a}R^{2b}$, —$C(O)R^{2a}$, —$C(O)OR^{2a}$, —$C(O)NR^{2a}R^{2b}$, —$SR^{2a}$, —$S(O)R^{2a}$, —$S(O)_2R^{2a}$, $C_{3-8}$ cycloalkyl, and $C_{3-8}$ heterocycloalkyl having from 1 to 3 heteroatoms each independently selected from the group consisting of N, O and S;

alternatively, two $R^2$ groups on adjacent ring atoms are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2c}$ groups;

$R^{2a}$, $R^{2b}$ and $R^{2c}$ are each independently selected from the group consisting of hydrogen and $C_{1-6}$ alkyl;

each $R^{3a}$ is independently halogen; and subscript n is an integer from 0 to 3;

or salts and isomers thereof.

In embodiments, the octahydro fused azadecalin compound has the formula:

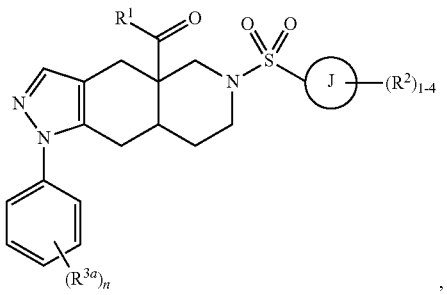

, wherein R¹ is selected from the group consisting of pyridine and thiazole, optionally substituted with 1-4 groups each independently selected from $R^{1a}$; each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, N-oxide, and $C_{3-8}$ cycloalkyl; ring J is selected from the group consisting of phenyl, pyridine, pyrazole, and triazole; each $R^2$ is independently selected from the group consisting of hydrogen, $C_{1-6}$ alkyl, halogen, $C_{1-6}$ haloalkyl, and —CN; $R^{3a}$ is F; subscript n is an integer from 0 to 3; or salts and isomers thereof.

Exemplary glucocorticoid receptor antagonists comprising an octohydro fused azadecalin structure include those described in U.S. Pat. No. 10,047,082. In embodiments, the octahydro fused azadecalin compound is the compound ((4aR,8aS)-1-(4-fluorophenyl)-6-((2-methyl-2H-1,2,3-triazol-4-yl)sulfonyl)-4,4a,5,6,7,8,8a,9-octahydro-1H-pyrazolo[3,4-g]isoquinolin-4a-yl)(4-(trifluoromethyl)pyridin-2-yl)methanone ("CORT125281") which has the structure:

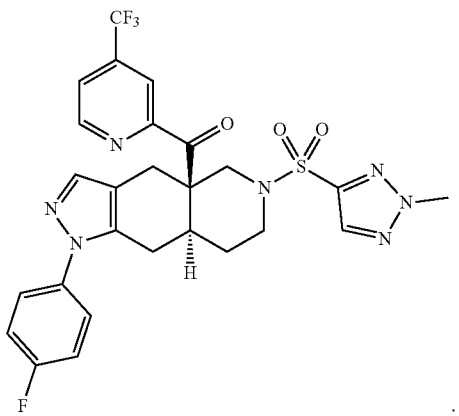 [SMILES: Cn1ncc(S(=O)(=O)N2CC[C@H]3Cc4c(cnn4-c4ccc(F)cc4)C[C@]3(C(=O)c3cc(C(F)(F)F)ccn3)C2)n1]

In embodiments, the GRM is the nonsteroidal octahydro fused azadecalin GRM compound having the chemical name ((4aR,8aS)-1-(4-fluorophenyl)-6-((2-isopropyl-2H-1,2,3-triazol-4-yl)sulfonyl)-4,4a,5,6,7,8,8a,9-octahydro-1H-pyrazolo[3,4-g]isoquinolin-4a-yl)(thiazol-2-yl)methanone, termed "CORT125329", having the formula:

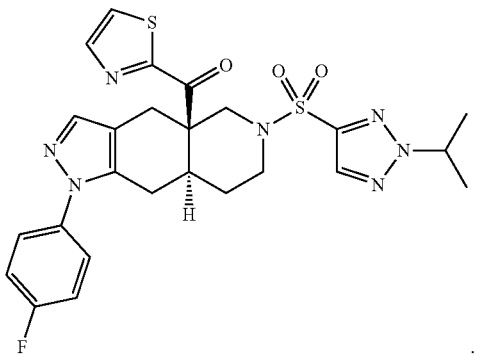 [SMILES: CC(C)n1ncc(S(=O)(=O)N2CC[C@H]3Cc4c(cnn4-c4ccc(F)cc4)C[C@]3(C(=O)c3nccs3)C2)n1]

To determine whether a test compound is a SGRM, the compound is first subjected to assays to measure its ability to bind to the GR and inhibit GR-mediated activities, which determines whether the compound is a glucocorticoid receptor modulator. The compound, if confirmed to be a glucocorticoid receptor modulator, is then subjected to a selectivity test to determine whether the compound can bind specifically to GR as compared to non-GR proteins, such as the estrogen receptor, the progesterone receptor, the androgen receptor, or the mineralocorticoid receptor. In one embodiment, a SGRM binds to GR at a substantially higher affinity, e.g., at least 10 times higher affinity, than to non-GR proteins. A SGRM may exhibit a 100-fold, 1000-fold or greater selectivity for binding to GR relative to binding to non GR proteins.

A test compound's ability to bind to the glucocorticoid receptor can be measured using a variety of assays, for example, by screening for the ability of the test compound to compete with a glucocorticoid receptor ligand, such as dexamethasone, for binding to the glucocorticoid receptor. Those of skill in the art will recognize that there are a number of ways to perform such competitive binding assays. In some embodiments, the glucocorticoid receptor is pre-incubated with a labeled glucocorticoid receptor ligand and then contacted with a test compound. This type of competitive binding assay may also be referred to herein as a binding displacement assay. A decrease of the quantity of labeled ligand bound to glucocorticoid receptor indicates that the test compound binds to the glucocorticoid receptor. In some cases, the labeled ligand is a fluorescently labeled compound (e.g., a fluorescently labeled steroid or steroid analog). Alternatively, the binding of a test compound to the glucocorticoid receptor can be measured directly with a labeled test compound. This latter type of assay is called a direct binding assay.

Both direct binding assays and competitive binding assays can be used in a variety of different formats. The formats may be similar to those used in immunoassays and receptor binding assays. For a description of different formats for binding assays, including competitive binding assays and direct binding assays, see *Basic and Clinical Immunology* 7th Edition (D. Stites and A. Terr ed.) 1991; *Enzyme Immunoassay*, E. T. Maggio, ed., CRC Press, Boca Raton, Fla. (1980); and "Practice and Theory of Enzyme Immunoassays," P. Tijssen, *Laboratory Techniques in Biochemistry and Molecular Biology*, Elsevier Science Publishers B.V. Amsterdam (1985), each of which is incorporated herein by reference.

In solid phase competitive binding assays, for example, the sample compound can compete with a labeled analyte for specific binding sites on a binding agent bound to a solid surface. In this type of format, the labeled analyte can be a glucocorticoid receptor ligand and the binding agent can be glucocorticoid receptor bound to a solid phase. Alternatively, the labeled analyte can be labeled glucocorticoid receptor and the binding agent can be a solid phase glucocorticoid receptor ligand. The concentration of labeled analyte bound to the capture agent is inversely proportional to the ability of a test compound to compete in the binding assay.

Alternatively, the competitive binding assay may be conducted in the liquid phase, and any of a variety of techniques known in the art may be used to separate the bound labeled protein from the unbound labeled protein. For example, several procedures have been developed for distinguishing between bound ligand and excess bound ligand or between bound test compound and the excess unbound test compound. These include identification of the bound complex by sedimentation in sucrose gradients, gel electrophoresis, or gel isoelectric focusing; precipitation of the receptor-ligand complex with protamine sulfate or adsorption on hydroxylapatite; and the removal of unbound compounds or ligands by adsorption on dextran-coated charcoal (DCC) or binding to immobilized antibody. Following separation, the amount of bound ligand or test compound is determined.

Alternatively, a homogenous binding assay may be performed in which a separation step is not needed. For example, a label on the glucocorticoid receptor may be altered by the binding of the glucocorticoid receptor to its ligand or test compound. This alteration in the labeled glucocorticoid receptor results in a decrease or increase in the signal emitted by label, so that measurement of the label at the end of the binding assay allows for detection or quantitation of the glucocorticoid receptor in the bound state. A wide variety of labels may be used. The component may be labeled by any one of several methods. Useful radioactive labels include those incorporating $^3$H, $^{125}$I, $^{35}$S, $^{14}$C, or $^{32}$P. Useful non-radioactive labels include those incorporating fluorophores, chemiluminescent agents, phosphorescent agents, electrochemiluminescent agents, and the like. Fluorescent agents are especially useful in analytical techniques that are used to detect shifts in protein structure such as fluorescence anisotropy and/or fluorescence polarization. The choice of label depends on sensitivity required, ease of conjugation with the compound, stability requirements, and available instrumentation. For a review of various labeling or signal producing systems which may be used, see U.S. Pat. No. 4,391,904, which is incorporated herein by reference in its entirety for all purposes. The label may be coupled directly or indirectly to the desired component of the assay according to methods well known in the art. In some cases, a test compound is contacted with a GR in the presence of a fluorescently labeled ligand (e.g., a steroid or steroid analog) with a known affinity for the GR, and the quantity of bound and free labeled ligand is estimated by measuring the fluorescence polarization of the labeled ligand.

ii. Activity

1) HepG2 Tyrosine Aminotransferase (TAT) Assay

Compounds that have demonstrated the desired binding affinity to GR are tested for their activity in inhibiting GR mediated activities. The compounds are typically subject to a Tyrosine Aminotransferase Assay (TAT assay), which assesses the ability of a test compound to inhibit the induction of tyrosine aminotransferase activity by dexamethasone. See Example 1. GR modulators that are suitable for the method disclosed herein have an $IC_{50}$ (half maximal inhibition concentration) of less than 10 micromolar. Other assays, including but not limited to those described below, can also be deployed to confirm the GR modulation activity of the compounds.

2) Cell-Based Assays

Cell-based assays which involve whole cells or cell fractions containing glucocorticoid receptors can also be used to assay for a test compound's binding or modulation of activity of the glucocorticoid receptor. Exemplary cell types that can be used according to the methods of the invention include, e.g., any mammalian cells including leukocytes such as neutrophils, monocytes, macrophages, eosinophils, basophils, mast cells, and lymphocytes, such as T cells and B cells, leukemia cells, Burkitt's lymphoma cells, tumor cells (including mouse mammary tumor virus cells), endothelial cells, fibroblasts, cardiac cells, muscle cells, breast tumor cells, ovarian cancer carcinomas, cervical carcinomas, glioblastomas, liver cells, kidney cells, and neuronal cells, as well as fungal cells, including yeast. Cells can be primary cells or tumor cells or other types of immortal cell lines. Of course, the glucocorticoid receptor can be expressed in cells that do not express an endogenous version of the glucocorticoid receptor.

In some cases, fragments of the glucocorticoid receptor, as well as protein fusions, can be used for screening. When molecules that compete for binding with the glucocorticoid receptor ligands are desired, the GR fragments used are fragments capable of binding the ligands (e.g., dexamethasone). Alternatively, any fragment of GR can be used as a target to identify molecules that bind the glucocorticoid receptor. Glucocorticoid receptor fragments can include any fragment of, e.g., at least 20, 30, 40, 50 amino acids up to a protein containing all but one amino acid of glucocorticoid receptor.

In some embodiments, a reduction in signaling triggered by glucocorticoid receptor activation is used to identify glucocorticoid receptor modulators. Signaling activity of the glucocorticoid receptor can be determined in many ways. For example, downstream molecular events can be monitored to determine signaling activity. Downstream events include those activities or manifestations that occur as a result of stimulation of a glucocorticoid receptor. Exemplary downstream events useful in the functional evaluation of transcriptional activation and antagonism in unaltered cells include upregulation of a number of glucocorticoid response element (GRE)-dependent genes (PEPCK, tyrosine amino transferase, aromatase). In addition, specific cell types susceptible to GR activation may be used, such as osteocalcin expression in osteoblasts which is downregulated by glucocorticoids; primary hepatocytes which exhibit glucocorticoid mediated upregulation of PEPCK and glucose-6-phosphate (G-6-Pase)). GRE-mediated gene expression has also been demonstrated in transfected cell lines using well-known GRE-regulated sequences (e.g., the mouse mammary tumor virus promoter (MMTV) transfected upstream of a reporter gene construct). Examples of useful reporter gene constructs include luciferase (luc), alkaline phosphatase (ALP) and chloramphenicol acetyl transferase (CAT). The functional evaluation of transcriptional repression can be carried out in cell lines such as monocytes or human skin fibroblasts. Useful functional assays include those that measure IL-1beta stimulated IL-6 expression; the downregulation of collagenase, cyclooxygenase-2 and various chemokines (MCP-1, RANTES); LPS stimulated cytokine release, e.g., TNFα; or expression of genes regulated by NFkB or AP-1 transcription factors in transfected cell-lines.

Compounds that are tested in whole-cell assays can also be tested in a cytotoxicity assay. Cytotoxicity assays are used to determine the extent to which a perceived effect is due to non-glucocorticoid receptor binding cellular effects. In an exemplary embodiment, the cytotoxicity assay includes contacting a constitutively active cell with the test compound. Any decrease in cellular activity indicates a cytotoxic effect.

Further illustrative of the many assays which can be used to identify compositions utilized in the methods of the invention, are assays based on glucocorticoid activities in vivo. For example, assays that assess the ability of a putative GR modulator to inhibit uptake of 3H-thymidine into DNA in cells which are stimulated by glucocorticoids can be used. Alternatively, the putative GR modulator can complete with 3H-dexamethasone for binding to a hepatoma tissue culture GR (see, e.g., Choi, et al., *Steroids* 57:313-318, 1992). As another example, the ability of a putative GR modulator to block nuclear binding of 3H-dexamethasone-GR complex can be used (Alexandrova et al., *J. Steroid Biochem. Mol. Biol.* 41:723-725, 1992). To further identify putative GR modulators, kinetic assays able to discriminate between glucocorticoid agonists and modulators by means of receptor-binding kinetics can also be used (as described in Jones, *Biochem J.* 204:721-729, 1982).

In another illustrative example, the assay described by Daune, Molec. Pharm. 13:948-955, 1977; and in U.S. Pat. No. 4,386,085, can be used to identify anti-glucocorticoid activity. Briefly, the thymocytes of adrenalectomized rats are incubated in nutritive medium containing dexamethasone with the test compound (the putative GR modulator) at varying concentrations. $^3$H-uridine is added to the cell culture, which is further incubated, and the extent of incorporation of radiolabel into polynucleotide is measured. Glucocorticoid agonists decrease the amount of $^3$H-uridine incorporated. Thus, a GR modulator will oppose this effect.

The GR modulators selected above are then subject to a selectivity assay to determine whether they are SGRMs. Typically, selectivity assays include testing a compound that binds glucocorticoid receptor in vitro for the degree of binding to non-glucocorticoid receptor proteins. Selectivity assays may be performed in vitro or in cell based systems, as described above. Binding may be tested against any appropriate non-glucocorticoid receptor protein, including antibodies, receptors, enzymes, and the like. In an exemplary embodiment, the non-glucocorticoid receptor binding protein is a cell-surface receptor or nuclear receptor. In another exemplary embodiment, the non-glucocorticoid receptor protein is a steroid receptor, such as estrogen receptor, progesterone receptor, androgen receptor, or mineralocorticoid receptor.

The selectivity of the antagonist for the GR relative to the MR can be measured using a variety of assays known to those of skill in the art. For example, specific antagonists can be identified by measuring the ability of the antagonist to bind to the GR compared to the MR (see, e.g., U.S. Pat. Nos. 5,606,021; 5,696,127; 5,215,916; 5,071,773). Such an analysis can be performed using either a direct binding assay or by assessing competitive binding to the purified GR or MR in the presence of a known ligand. In an exemplary assay, cells that stably express the glucocorticoid receptor or mineralocorticoid receptor (see, e.g., U.S. Pat. No. 5,606,021) at high levels are used as a source of purified receptor. The affinity of the ligand for the receptor is then directly measured. Those GR modulators that exhibit at least a 10 fold, 100-fold higher affinity, often 1000-fold, for the GR relative to the MR are then selected for use in the methods of the invention.

The selectivity assay may also include assaying the ability to inhibit GR-mediated activities, but not MR-mediated activities. One method of identifying such a GR-specific modulator is to assess the ability of an antagonist to prevent activation of reporter constructs using transfection assays (see, e.g., Bocquel et al, J. Steroid Biochem Molec. Biol. 45:205-215, 1993; U.S. Pat. Nos. 5,606,021, 5,929,058). In an exemplary transfection assay, an expression plasmid encoding the receptor and a reporter plasmid containing a reporter gene linked to receptor-specific regulatory elements are cotransfected into suitable receptor-negative host cells. The transfected host cells are then cultured in the presence and absence of a hormone, such as cortisol or an analog thereof, able to activate the hormone responsive promoter/enhancer element of the reporter plasmid. Next the transfected and cultured host cells are monitored for induction (i.e., the presence) of the product of the reporter gene sequence. Finally, the expression and/or steroid binding-capacity of the hormone receptor protein (coded for by the receptor DNA sequence on the expression plasmid and produced in the transfected and cultured host cells), is measured by determining the activity of the reporter gene in the presence and absence of an antagonist. The antagonist activity of a compound may be determined in comparison to known antagonists of the GR and MR receptors (see, e.g., U.S. Pat. No. 5,696,127). Efficacy is then reported as the percent maximal response observed for each compound relative to a reference antagonist compound. GR modulators that exhibits at least a 100-fold, often 1000-fold or greater, activity towards the GR relative to the MR, PR, or AR are then selected for use in the methods disclosed herein.

An exemplar nonsteroidal SGRM that can be used in the methods disclosed herein is relacorilant, i.e., (R)-(1-(4-fluorophenyl)-6-((1-methyl-1H-pyrazol-4-yl)sulfonyl)-4,4a, 5,6,7,8-hexahydro-1H-pyrazol o[3,4-g]isoquinolin-4a-yl) (4-(trifluoromethyl)pyridin-2-yl)methanone, which has the following structure:

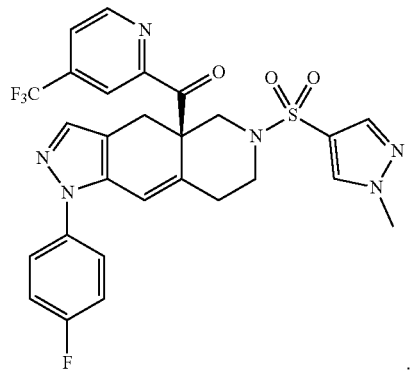 [SMILES: Cn1cc(S(=O)(=O)N2CCC3=Cc4c(cnn4-c4ccc(F)cc4)C[C@]3(C(=O)c3cc(C(F)(F)F)ccn3)C2)cn1]

PHARMACEUTICAL COMPOSITIONS AND ADMINISTRATION

In embodiments, the present invention provides a pharmaceutical composition for treating cortisol excess, the pharmaceutical composition including a pharmaceutically acceptable excipient and a GRM. In some embodiments, the pharmaceutical composition includes a pharmaceutically acceptable excipient and a SGRM. In preferred embodiments, the pharmaceutical composition includes a pharmaceutically acceptable excipient and a nonsterodial SGRM.

GRMs and SGRMs (as used herein, GRMs and SGRMs include nonsteroidal GRMs and nonsteroidal SGRMS), can be prepared and administered in a wide variety of oral, parenteral and topical dosage forms. Oral preparations include tablets, pills, powder, dragees, capsules, liquids, lozenges, gels, syrups, slurries, suspensions, etc., suitable for ingestion by the patient. GRMs and SGRMs can also be administered by injection, that is, intravenously, intramuscularly, intracutaneously, subcutaneously, intraduodenally, or intraperitoneally. Also, GRMs and SGRMs can be administered by inhalation, for example, intranasally. Additionally, GRMs and SGRMs can be administered transdermally. Accordingly, the present invention also provides pharmaceutical compositions including a pharmaceutically acceptable carrier or excipient and a GRM or SGRM.

For preparing pharmaceutical compositions from GRMs and SGRMs, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component, a GRM or SGRM. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Suitable solid excipients are carbohydrate or protein fillers include, but are not limited to sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain GR modulator mixed with a filler or binders such as lactose or starches, lubricants such as talc or magnesium stearate, and, optionally, stabilizers. In soft capsules, the GR modulator compounds may be dissolved or suspended in suitable liquids, such as fatty oils, liquid paraffin, or liquid polyethylene glycol with or without stabilizers.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending a SGRM in a vegetable oil, such as *arachis* oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

GRMs and SGRMs can be delivered by transdermally, by a topical route, formulated as applicator sticks, solutions, suspensions, emulsions, gels, creams, ointments, pastes, jellies, paints, powders, and aerosols.

GRMs and SGRMs can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

The pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

In another embodiment, the formulations of the invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the GR modulator into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

The pharmaceutical preparation is preferably in unit dosage form. In such form the preparation is subdivided into unit doses containing appropriate quantities of the active component, a GRM or SGRM. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 6000 mg, most typically 50 mg to 500 mg. Suitable dosages also include about 1 mg, 5, 10, 20, 30, 40, 50, 60, 70, 80, 90, 100, 200, 300, 400, 500, 600, 700, 800, 900, 1000, 1100, 1200, 1300, 1400, 1500, 1600, 1700, 1800, 1900, or 2000 mg, according to the particular application and the potency of the active component. The composition can, if desired, also contain other compatible therapeutic agents.

In some cases, the effective amount of the GRM (e.g., a relacorilant) is a daily dose of between 1 and 100 mg/kg/day. In some embodiments, the daily dose of the GRM is 1, 2, 4, 6, 8, 10, 12, 14, 16, 18, 20, 30, 40, 50 60, 70, 80, 90 or 100 mg/kg/day. In some cases, the GRM is administered for at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, or 80 weeks.

Single or multiple administrations of formulations can be administered depending on the dosage and frequency as required and tolerated by the patient. The formulations should provide a sufficient quantity of active agent to effectively treat the disease state. Thus, in one embodiment, the pharmaceutical formulation for oral administration of a GRM is in a daily amount of between about 0.01 to about 150 mg per kilogram of body weight per day (mg/kg/day). In some embodiments, the daily amount is from about 1.0 to 100 mg/kg/day, 5 to 50 mg/kg/day, 10 to 30 mg/kg/day, and 10 to 20 mg/kg/day. Lower dosages can be used, particularly when the drug is administered to an anatomically secluded site, such as the cerebral spinal fluid (CSF) space, in contrast to administration orally, into the blood stream, into a body cavity or into a lumen of an organ. Substantially higher dosages can be used in topical administration. Actual methods for preparing parenterally administrable formulations will be known or apparent to those skilled in the art and are described in more detail in such publications as Remington's, supra. See also Nieman, In "Receptor Mediated Antisteroid Action," Agarwal, et al., eds., De Gruyter, N.Y. (1987).

The duration of treatment with a GRM or SGRM to reduce the cortisol excess can vary according to the severity of the condition in a subject and the subject's response to GRMs or SGRMs. In some embodiments, GRMs and SGRMs can be administered for a period of about 1 week to 104 weeks (2 years), more typically about 6 weeks to 80 weeks, most typically about 9 to 60 weeks. Suitable periods of administration also include 5 to 9 weeks, 5 to 16 weeks, 9 to 16 weeks, 16 to 24 weeks, 16 to 32 weeks, 24 to 32 weeks, 24 to 48 weeks, 32 to 48 weeks, 32 to 52 weeks, 48 to 52 weeks, 48 to 64 weeks, 52 to 64 weeks, 52 to 72 weeks, 64 to 72 weeks, 64 to 80 weeks, 72 to 80 weeks, 72 to 88 weeks, 80 to 88 weeks, 80 to 96 weeks, 88 to 96 weeks, and 96 to 104 weeks. Suitable periods of administration also include 5, 6, 7, 8, 9, 10, 11, 12, 13, 14, 15, 16, 17, 18, 19, 20, 24, 25, 30, 32, 35, 40, 45, 48 50, 52, 55, 60, 64, 65, 68, 70, 72, 75, 80, 85, 88 90, 95, 96, 100, and 104 weeks. Generally administration of a GRM or SGRM should be continued until clinically significant reduction or amelioration is observed. Treatment with the GRM or SGRM in accordance with the invention may last for as long as two years or even longer.

In some embodiments, administration of a GRM or SGRM is not continuous and can be stopped for one or more periods of time, followed by one or more periods of time where administration resumes. Suitable periods where administration stops include 5 to 9 weeks, 5 to 16 weeks, 9 to 16 weeks, 16 to 24 weeks, 16 to 32 weeks, 24 to 32 weeks, 24 to 48 weeks, 32 to 48 weeks, 32 to 52 weeks, 48 to 52 weeks, 48 to 64 weeks, 52 to 64 weeks, 52 to 72 weeks, 64 to 72 weeks, 64 to 80 weeks, 72 to 80 weeks, 72 to 88 weeks, 80 to 88 weeks, 80 to 96 weeks, 88 to 96 weeks, and 96 to 100 weeks. Suitable periods where administration stops also include 5, 6, 7, 8, 9, 10, 11, 12, 13, 14, 15, 16, 17, 18, 19, 20, 24, 25, 30, 32, 35, 40, 45, 48 50, 52, 55, 60, 64, 65, 68, 70, 72, 75, 80, 85, 88 90, 95, 96, and 100 weeks.

The dosage regimen also takes into consideration pharmacokinetics parameters well known in the art, i.e., the rate of absorption, bioavailability, metabolism, clearance, and the like (see, e.g., Hidalgo-Aragones (1996) *J. Steroid Biochem. Mol. Biol.* 58:611-617; Groning (1996) *Pharmazie* 51:337-341; Fotherby (1996) *Contraception* 54:59-69; Johnson (1995) *J. Pharm. Sci.* 84:1144-1146; Rohatagi (1995) *Pharmazie* 50:610-613; Brophy (1983) *Eur. J Clin. Pharmacol.* 24:103-108; the latest Remington's, supra). The state of the art allows the clinician to determine the dosage regimen for each individual patient, GR modulator and disease or condition treated.

SGRMs can be used in combination with other active agents known to be useful in modulating a glucocorticoid receptor, or with adjunctive agents that may not be effective alone, but may contribute to the efficacy of the active agent.

In some embodiments, co-administration includes administering one active agent, a GRM or SGRM, within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

After a pharmaceutical composition including a GR modulator of the invention has been formulated in an acceptable carrier, it can be placed in an appropriate container and labeled for treatment of an indicated condition.

For administration of a GRM or SGRM, such labeling would include, e.g., instructions concerning the amount, frequency and method of administration.

The pharmaceutical compositions of the present invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

In another embodiment, the compositions of the present invention are useful for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

I. Combination Therapies

Various combinations with a GRM or SGRM and another pharmaceutical agent (which may be a small molecule drug, an large molecule such as an antibody or peptide, or may be an immunotherapy agent, or a cancer chemotherapy agent, or a combination of such agents and compounds) may be employed to treat a patient. By "combination therapy" or "in combination with", it is not intended to imply that the therapeutic agents must be administered at the same time and/or formulated for delivery together, although these methods of delivery are within the scope described herein. The GRM or SGRM and the pharmaceutical agent can be administered following the same or different dosing regimen. In some embodiments, the GRM or SGRM and the pharmaceutical agent is administered sequentially in any order during the entire or portions of the treatment period. In some embodiments, the GRM or SGRM and the other therapeutic agent is administered simultaneously or approximately simultaneously (e.g., within about 1, 5, 10, 15, 20, or 30 minutes of each other). Non-limiting examples of combination therapies are as follows, with administration of the GRM or SGRM and other therapeutic agent for example, GRM or SGRM is "A" and other therapeutic agent or compound, given as part of therapeutic regime, is "B":

A/B/AB/A/BB/B/AA/A/BA/B/BB/A/AA/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of the therapeutic compounds or agents to a patient will follow general protocols for the administration of such compounds, taking into account the toxicity, if any, of the therapy. Surgical intervention may also be applied in combination with the described therapy.

The present methods can be combined with other means of treatment such as surgery, radiation, targeted therapy, immunotherapy, use of growth factor inhibitors, or anti-angiogenesis factors.

All patents, patent publications, publications, and patent applications cited in this specification are hereby incorporated by reference herein in their entireties as if each individual publication or patent application were specifically and individually indicated to be incorporated by reference.

EXAMPLES

The following examples are provided by way of illustration only and not by way of limitation. Those of skill will readily recognize a variety of noncritical parameters which could be changed or modified to yield essentially similar results.

Example 1. HEPG2 Tyrosine Aminotransferase (Tat) Assay

The following protocol describes an assay for measuring induction of TAT by dexamethasone in HepG2 cells (a human liver hepatocellular carcinoma cell line; ECACC, UK). HepG2 cells are cultured using MEME media supplemented with 10% (v/v) foetal bovine serum; 2 mM L-glutamine and 1% (v/v) NEAA at 37° C., 5%/95% (v/v) $CO_2$/air. The HepG2 cells are then be counted and adjusted to yield a density of $0.125 \times 10^6$ cells/ml in RPMI 1640 without phenol red, 10% (v/v) charcoal stripped FBS, 2 mM L-glutamine and seeded at 25,000 cells/well in 200 μl into 96 well, sterile, tissue culture micro titre plates, and incubated at 37° C., 5% $CO_2$ for 24 hours.

Growth media are then removed and replaced with assay media {RPMI 1640 without phenol red, 2 mM L-glutamine+ 10 μM forskolin}. Test compounds are then screened against a challenge of 100 nM dexamethasone. Compounds are then be serially half log diluted in 100% (v/v) dimethylsupfoxide from a 10 mM stock. Then an 8-point half-log dilution curve are generated followed by a 1:100 dilution into assay media to give a 10× final assay of the compound concentration, this results in final assay of the compound concentration that ranged 10 to 0.003 μM in 0.1% (v/v) dimethylsulfoxide.

Test compounds are pre-incubated with cells in microtitre plates for 30 minutes at 37° C., 5/95 (v/v) $CO_2$/air, before the addition of 100 nM dexamethasone and then subsequently for 20 hours to allow optimal TAT induction.

HepG2 cells are then lysed with 30 μl of cell lysis buffer containing a protease inhibitor cocktail for 15 minutes at 4° C. 155 μl of substrate mixture can then be added containing 5.4 mM Tyrosine sodium salt, 10.8 mM alpha ketoglutarate and 0.06 mM pyridoxal 5' phosphate in 0.1M potassium phosphate buffer (pH 7.4). After 2 hours incubation at 37° C. the reaction can be terminated by the addition of 15 µl of 10M aqueous potassium hydroxide solution, and the plates incubated for a further 30 minutes at 37° C. The TAT activity product can be measured by absorbance at λ 340 nm.

$IC_{50}$ values can be calculated by plotting % inhibition (normalised to 100 nM dexamethasone TAT stimulation) v. compound concentration and fitting the data to a 4 parameter logistic equation. $IC_{50}$ values can converted to Ki (equilibrium dissociation constant) using the Cheng and Prusoff equation, assuming the antagonists were competitive inhibitors with respect to dexamethasone.

Example 2. Clinical Responses to Relacorilant

Responses to Relacorilant in Healthy Subjects

Studies of relacorilant in human volunteers have shown that daily dosing results in achievement of steady state levels by Day 7. Single doses of from 5 mg to 500 mg of relacorilant are well-tolerated in human subjects, as are 14 days of relacorilant dosing at doses of 50 mg, 150 mg, and 250 mg as well. Some subjects reported mild to moderate musculoskeletal AEs with repeat doses up to 250 mg. A transient reduction in platelet count was observed in some subjects in a non-dose-dependent manner; this resolved by study end. In addition, some subjects received 500-mg relacorilant. Some subjects reported (non-serious) musculoskeletal adverse events.

Example 3. Clinical Responses to Relacorilant

Responses to Relacorilant in Cushing's Syndrome Patients

Relacorilant was administered to (or self-administered by) male and female fasting Cushing's syndrome patients (n=35) (in multiple capsules each containing 50 milligrams (mg) of relacorilant) orally once per day (in the morning with no food for 4 hours before and 1 hour after dosing). The patients had a confirmed diagnosis of endogenous Cushing's syndrome and at least one of the following: a) Type 2 diabetes or impaired glucose tolerance, and b) uncontrolled or untreated hypertension. All patients gave informed consent before participating in any study-related procedures.

The patients received daily doses of relacorilant at their initial dose for four weeks, after which the daily dose was increased in 50 mg increments, as tolerable, every four weeks. The first 17 patients to enroll (Group 1, the "low-dose cohort", LD) received 100 mg relacorilant per day for 4 weeks, then 150 mg relacorilant per day for 4 weeks, then 200 mg relacorilant per day for 4 weeks (12 weeks total). The next 18 patients (Group 2, the "high dose cohort", HD) started at 250 mg relacorilant per day; this was increased to 300 mg relacorilant per day after four weeks, and then to 350 mg relacorilant per day following four weeks at 300 mg per day, and finally, where tolerated, after four weeks at 350 mg per day, the daily dose was increased to 400 mg relacorilant per day for a final four weeks (16 weeks total).

The study protocol called for patient visits to the study site at screening, on Day 1 (baseline), Weeks 2, 4, 6, 8, 10, and 12, and after a 4-week follow-up period for Group 1. For Group 2, the protocol called for patient visits to the study site at screening, on Day 1 (baseline), Weeks 2, 4, 6, 8, 10, 12, 14, and 16, and after a 4-week follow-up period. Patient dosing will be done at home, except on days of study visits.

Patient monitoring during the study included monitoring of blood levels of relacorilant and its metabolites measured predose and at 1, 2, 4, 6, and 8 hours postdose at Weeks 2, 6, and 10, and predose only at Weeks 4, 8, and 12/early termination (ET) (for patients in Group 1). For patients in Group 2, blood levels of relacorilant and its metabolites were measured predose and at 1, 2, 4, 6, and 8 hours postdose at Weeks 2, 6, 10, and 14 and predose only at Weeks 4, 8, 12, and 16/early termination (ET). The safety protocol also included assessments by physical examination findings, vital signs, ECG results, pregnancy tests, clinical laboratory test results (hematology and chemistry panels), adverse events (AEs), and concomitant medications. Safety and pharmacokinetic (PK) data were reviewed to confirm the appropriateness of the administered dose levels, including following escalation to higher doses (i.e., 2 weeks following dose escalation to 200 mg/day), and when steady-state PK data were available for 6 patients who reached their highest relacorilant dose (e.g., Week 10 for 350 mg relacorilant daily doses and Week 14 for 400 mg relacorilant daily doses) and at the end of the study.

Response criteria for hyperglycemia were changes from baseline in glucose tolerance as measured by: ≥0.5% decrease in HbAlc, normalization or ≥50 mg/dL decrease in 2-hr OGTT glucose, or decrease in total daily insulin (≥25%) or sulfonylurea dose (≥50%). Response criteria for hypertension (HTN) was a ≥5 mm Hg decrease in mean systolic and/or diastolic blood pressure (SBP/DBP).

In this study, regarding the high dose cohort (Group 2), fifty percent of patients with hyperglycemia achieved improved glucose control, as shown by (i) a 0.5 percent or greater reduction in HbAlc or (ii) normalization of 2-hour oGTT glucose or decreased by at least 50 mg/dL or (iii) a 25 percent decrease in antidiabetic medications. Sixty-four percent of patients with uncontrolled hypertension achieved a five millimeter or greater drop in either systolic or diastolic blood pressure, as measured by 24-hour ambulatory monitoring. Patients in the high-dose group also met a wide range of secondary endpoints, including statistically significant improvements in hypercoagulopathy, liver function, serum osteocalcin (a marker of bone formation), cognitive function, depression and quality of life.

Therapeutic improvements noted in at least some patients included improvements in blood clotting measures indicating improvement in hypercoagulopathy and lessening of risk of embolism; improvements in other blood indicators (e.g., platelet count and others); improvement in indicators of heart function and heart rhythm (e.g., improvement in abnormalities of cardiac function, improvement in indicators of left ventricular hypertrophy; improvements in measures of liver function; improvements in measures of immune system function and status; improvements in measures of bone health; improvements in patients' quality of life; improvements in patients' pyschological well-being (e.g., lessening of depression); and improvements in patients' glucose levels suggesting improvement in, or lessening risk of, metabolic syndrome, pre-diabetes or diabetes.

These and further results are presented in TABLE 1.

Relacorilant was well-tolerated by these patients. There was no evidence of relacorilant having any progesterone receptor affinity; and none of the patients suffered hypokalemia. There were no drug-related serious adverse events.

Figure 2:
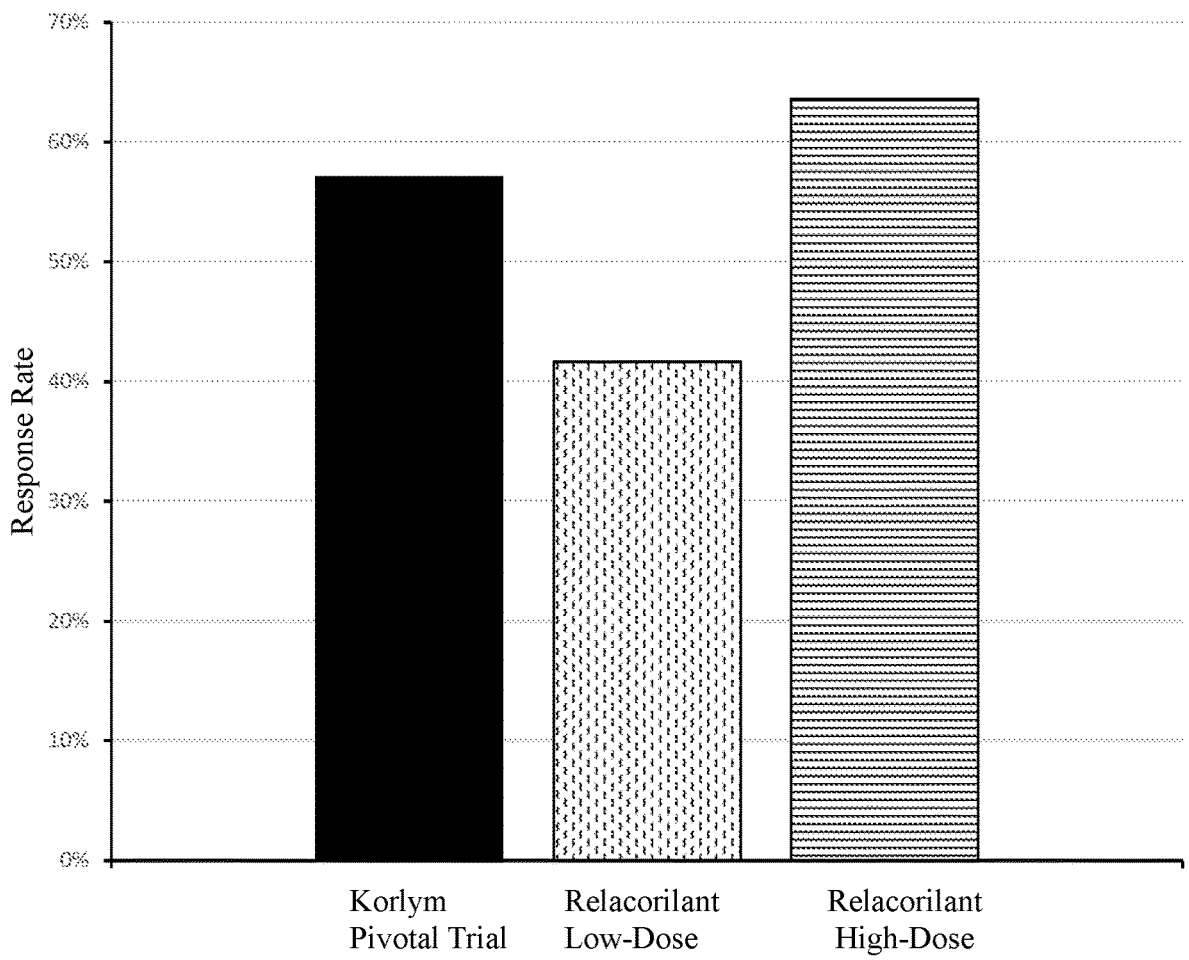
FIG. 2 Patients achieving clinically meaningful improvements in hypertension (high blood pressure).
Figure 3:
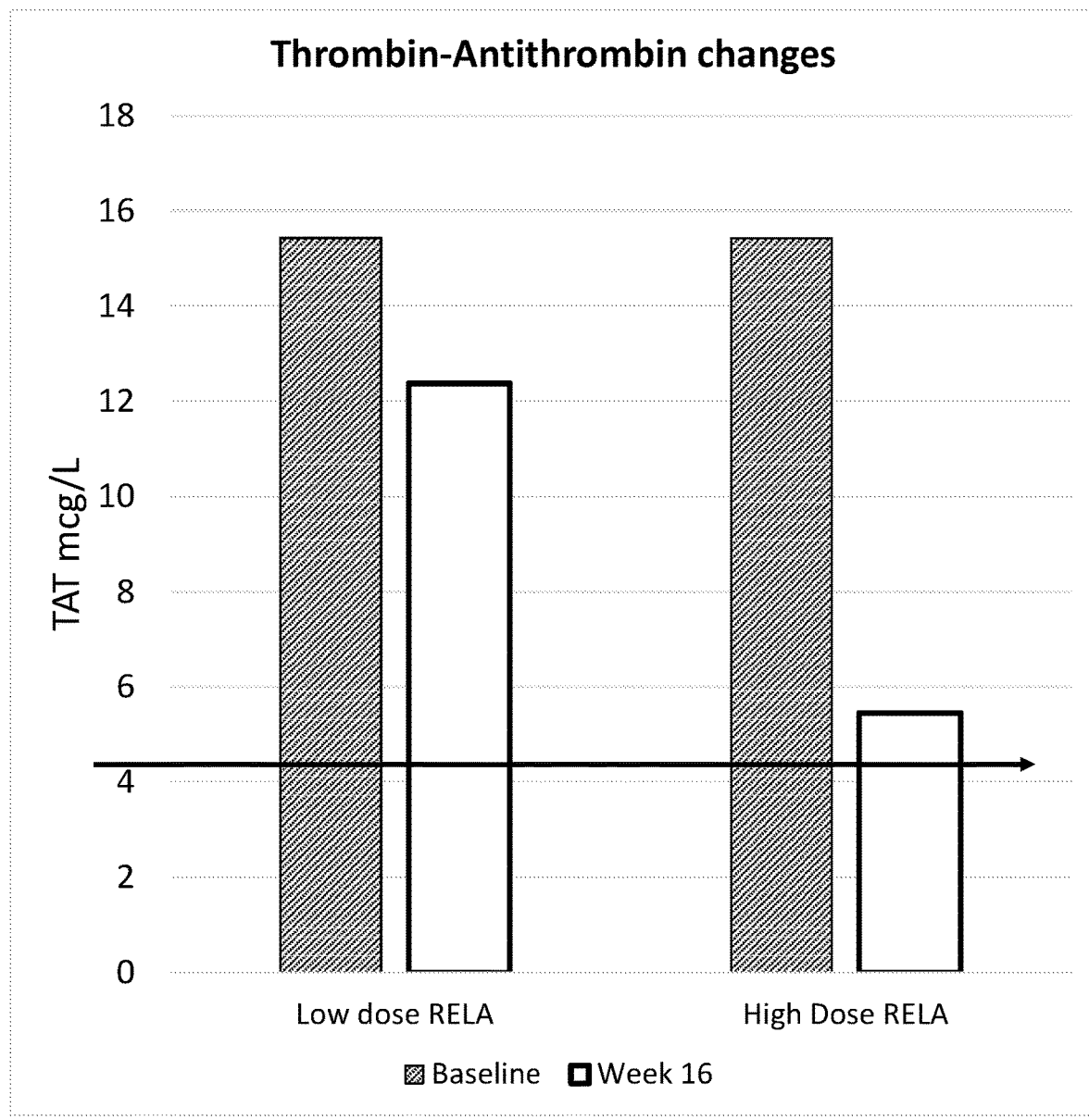
FIG. 3 Relacorilant effects on Coagulation: There is a high risk of thrombotic events in patients with Cushing's syndrome; Cushing's syndrome patients treated with relacorilant showed improvement in coagulation factors. This result indicates that relacorilant may be useful to improve pre-operative coagulation control (before surgery for Cushing's syndrome) in Cushing's syndrome patients at high risk of thrombotic events.

FIG. 1 illustrates the improvement in glucose control resulting from relacorilant administration. 50 percent of patients with hyperglycemia in the high-dose cohort achieved improved glucose control (see FIG. 1). The response rate in patients with hypertension was 64 percent (see FIG. 2). These response rates are comparable to those exhibited by patients at 16 weeks and a dose of 1200 mg in Korlym's pivotal trial (e.g., Fleseriu et al, J. Clin. Endocrinol. Metab. 97(6):2039-2049 (2012); Fleseriu et al., J Clin Endocrinol Metab, 99(10):3718-3727 (2014).

Clinical results of the study are presented in Table 1. Results are reported for the modified intent to treat population (mITT) and the modified protocol population (modified per protocol: mPP); intention to treat (ITT) analysis includes every subject who is randomized according to randomized treatment assignment. It ignores noncompliance, protocol deviations, withdrawal, and anything that happens after randomization. In contrast, per-protocol (PP) analysis refers to inclusion in the analysis of only those patients who strictly adhered to the protocol. The PP analysis provides an estimate of the true efficacy of an intervention, i.e., among those who completed the treatment as planned.

TABLE 1

Means and Wilcoxon Signed Rank P-values for Key Outcomes by Group and Population for Change from Baseline to Last Observed (mITT and mPP)

| Category | Parameter | Population | Group 1 Mean | Group 1 P-Value | Group 2 Mean | Group 2 P-Value | Overall Mean | Overall P-Value |
|---|---|---|---|---|---|---|---|---|
| Abnormal at Baseline | Factor IX (%) | mITT | −40.8 | 0.0625 | −4.2 | 0.8125 | −22.5 | 0.0293 |
| | | mPP | −40.8 | 0.0625 | −4.2 | 0.8125 | −22.5 | 0.0293 |
| | Factor X (%) | mITT | −15.8 | 0.0625 | −22 | 0.2500 | −18.13 | 0.0078 |
| | | mPP | −15.8 | 0.0625 | −22 | 0.2500 | −18.13 | 0.0078 |
| | Thrombin-Antithrombin (mcg/L) | mITT | 1.61 | 0.6484 | −9.83 | 0.0923 | −3.88 | 0.5469 |
| | | mPP | 1.61 | 0.6484 | −9.83 | 0.0923 | −3.88 | 0.5469 |
| | von Willebrand Factor (%) | mITT | | | −18.5 | 0.3125 | −18.5 | 0.3125 |
| | | mPP | | | −18.5 | 0.3125 | −18.5 | 0.3125 |
| All Subjects | ALT (SGPT) (U/L) | mITT | −7.88 | 0.0105 | −13.35 | 0.0002 | −10.62 | <0.0001 |
| | AST (SGOT) (U/L) | mITT | −2.71 | 0.1663 | −7.31 | 0.0039 | −4.94 | 0.0013 |
| | AUCglucose (hr*mmol/L) | mITT | −3.11 | 0.0171 | −0.8 | 0.4973 | −1.96 | 0.0214 |
| | | mPP | −3.63 | 0.0171 | −1.24 | 0.3394 | −2.48 | 0.0097 |
| | AUCinsulin (hr*µU/mL) | mITT | −33.28 | 0.1465 | −32.26 | 0.7354 | −32.77 | 0.2348 |
| | | mPP | −38.79 | 0.1677 | −37.39 | 0.5693 | −38.12 | 0.2075 |
| | Absolute Eosinophils ($10^9$ | mITT | 0.05 | 0.0073 | 0.05 | 0.2686 | 0.05 | 0.0060 |
| | Absolute Lymphocytes ($10^9$ | mITT | −0.15 | 0.4874 | 0.26 | 0.0225 | 0.05 | 0.3778 |
| | BDI-II Total Score | mITT | −3.06 | 0.2096 | −3.94 | 0.0056 | −3.48 | 0.0044 |
| | | mPP | −4.47 | 0.1479 | −3.87 | 0.0083 | −4.19 | 0.0047 |
| | Cushing QOL Score | mITT | 6.25 | 0.0186 | 8.07 | 0.0636 | 7.13 | 0.0024 |
| | | mPP | 6.25 | 0.0186 | 7.64 | 0.1050 | 6.9 | 0.0042 |
| | ECG Median Heart Rate (beats/min) | Safety | 8 | 0.0505 | 5.23 | 0.2078 | 6.7 | 0.0111 |
| | | mITT | 8 | 0.0505 | 5.23 | 0.2078 | 6.7 | 0.0111 |
| | Factor IX (%) | mITT | −11.59 | 0.1475 | 6.44 | 0.3964 | −2.85 | 0.5578 |
| | | mPP | −11.59 | 0.1475 | 6.44 | 0.3964 | −2.85 | 0.5578 |
| | Factor VIII (%) | mITT | −11.94 | 0.2385 | −26.38 | 0.0492 | −18.94 | 0.0219 |
| | | mPP | −11.94 | 0.2385 | −26.38 | 0.0492 | −18.94 | 0.0219 |
| | Factor X (%) | mITT | −0.06 | 0.9914 | −8.88 | 0.0033 | −4.33 | 0.0672 |
| | | mPP | −0.06 | 0.9914 | −8.88 | 0.0033 | −4.33 | 0.0672 |
| | Fructosamine (µmol/L), IGT | mITT | −6.85 | 0.2749 | −21.58 | 0.0010 | −13.92 | 0.0021 |
| | | mPP | −8.08 | 0.1812 | −18.92 | 0.0098 | −13.28 | 0.0052 |
| | HOMA-IR, IGT | mITT | 0.05 | 0.6355 | −3.2 | 0.0327 | −1.58 | 0.0642 |
| | | mPP | 0.39 | 0.7354 | −3.28 | 0.0923 | −1.37 | 0.1383 |
| | POMC and proACTH (pmol/L) | mITT | | | 7.91 | 0.0234 | 7.91 | 0.0234 |
| | | mPP | | | 7.91 | 0.0234 | 7.91 | 0.0234 |
| | PR Interval, Aggregate (msec) | Safety | 2.72 | 0.3778 | −4.2 | 0.1726 | −0.4 | 0.9238 |
| | | mITT | 2.72 | 0.3778 | −4.2 | 0.1726 | −0.4 | 0.9238 |
| | Part A - Total Time to Complete T | mITT | −3.65 | 0.1534 | −4.67 | 0.0079 | −4.13 | 0.0030 |
| | | mPP | −3.65 | 0.1534 | −4.67 | 0.0079 | −4.13 | 0.0030 |
| | Part B - Total Time to Complete T | mITT | −15.94 | 0.0552 | −34.6 | <0.0001 | −24.69 | <0.0001 |
| | | mPP | −15.94 | 0.0552 | −34.6 | <0.0001 | −24.69 | <0.0001 |
| | Platelet Count ($10^9$/L) | mITT | −62.82 | 0.0003 | −74.82 | 0.0002 | −68.82 | <0.0001 |
| | QRS Duration, Aggregate (msec) | Safety | −0.79 | 0.4510 | −0.77 | 0.5416 | −0.78 | 0.2884 |
| | | mITT | −0.79 | 0.4510 | −0.77 | 0.5416 | −0.78 | 0.2884 |
| | QT Interval, Aggregate (msec) | Safety | −15.85 | 0.0505 | −11.04 | 0.3028 | −13.6 | 0.0159 |
| | | mITT | −15.85 | 0.0505 | −11.04 | 0.3028 | −13.6 | 0.0159 |
| | QTcB Interval, Aggregate (msec) | Safety | 5.58 | 0.2247 | 2.28 | 0.8040 | 4.03 | 0.2685 |
| | | mITT | 5.58 | 0.2247 | 2.28 | 0.8040 | 4.03 | 0.2685 |
| | QTcF Interval, | Safety | −1.98 | 0.5477 | −2.54 | 0.9780 | −2.24 | 0.6214 |

TABLE 1-continued

Means and Wilcoxon Signed Rank P-values for Key Outcomes by Group and
Population for Change from Baseline to Last Observed (mITT and mPP)

| Category | Parameter | Population | Group 1 Mean | Group 1 P-Value | Group 2 Mean | Group 2 P-Value | Overall Mean | Overall P-Value |
|---|---|---|---|---|---|---|---|---|
| | Aggregate (msec) | mITT | −1.98 | 0.5477 | −2.54 | 0.9780 | −2.24 | 0.6214 |
| | RR Interval, | Safety | −93.14 | 0.0202 | −56.67 | 0.2524 | −76.04 | 0.0081 |
| | Aggregate (msec) | mITT | −93.14 | 0.0202 | −56.67 | 0.2524 | −76.04 | 0.0081 |
| | Serum Bone | mITT | 1.82 | 0.0957 | −1.09 | 0.1329 | 0.41 | 0.7866 |
| | Alkaline Phosphatase ( | mPP | 1.82 | 0.0957 | −1.09 | 0.1329 | 0.41 | 0.7866 |
| | Serum | mITT | 4.57 | 0.0161 | 1.33 | 0.2129 | 3 | 0.0097 |
| | Osteocalcin (µg/L) | mPP | 4.68 | 0.0080 | 1.33 | 0.2129 | 3.06 | 0.0069 |
| | Thrombin- | mITT | 1.48 | 0.3843 | −7.13 | 0.2979 | −2.69 | 0.9930 |
| | Antithrombin (mcg/L) | mPP | 1.48 | 0.3843 | −7.13 | 0.2979 | −2.69 | 0.9930 |
| | Urinary NTx | mITT | 2.21 | 0.3906 | 0.63 | 0.7928 | 1.37 | 0.4521 |
| | (mnolBCE/mmol) | mPP | 2.21 | 0.3906 | 0.63 | 0.7928 | 1.37 | 0.4521 |
| | aPTT (sec) | mITT | 2.24 | 0.2820 | 0.5 | 0.1191 | 1.45 | 0.0456 |
| | | mPP | 2.24 | 0.2820 | 0.5 | 0.1191 | 1.45 | 0.0456 |
| | von | mITT | 2.88 | 0.9632 | 10.88 | 0.6413 | 6.76 | 0.6812 |
| | Willebrand Factor (%) | mPP | 2.88 | 0.9632 | 10.88 | 0.6413 | 6.76 | 0.6812 |

These results show a statistically significant reduction in the $AUC_{glucose}$ in patients with hyperglycemia. Response rates were 15.4% in the LD group and 50% in the HD group by weeks 12 and 16, respectively. Response rates for hypertension were 41.7% in the LD group and 63.6% in the HD group by weeks 12 and 16, respectively. In addition to these primary endpoints, significant changes in various secondary endpoints related to cortisol excess were seen, including improvements in hypercoagulopathy, liver function, insulin sensitivity, cognitive function, depression, and Cushing quality of life (QoL) score. Some weight loss was observed in many of the patients. The most common treatment-emergent adverse events (TEAEs) were back pain, edema, headache, and nausea. Five serious TEAEs were reported in 4 patients. The serious TEAEs were all from the HD group and were related primarily to the unmasking of chronic conditions that were suppressed from chronic cortisol excess. No drug-induced hypokalemia or vaginal bleeding were seen in the study.

These results show that relacorilant is effective in reducing many of the effects of excess cortisol in Cushing's syndrome patients. Thus, relacorilant treatment is believed to be useful for treating Cushing's syndrome. In addition, relacorilant is believed to be useful for treating fatty liver diseases (see, e.g., the ALT, AST, HOMA, and other measures in Table 1). Furthermore, relacorilant is believed to be useful for treating bone disorders (see, e.g., the serum osteocalcin measure in Table 1). Relacorilant is further believed to be useful for treating heart ailments, including left ventricular hypertrophy, arrhythmias, and other forms of heart disease (see, e.g., the heart measures such as QT in Table 1). In addition, relacorilant is believed to be useful for treating blood clotting disorders, depression, and for improving patients' quality of life. Relacorilant may be useful in combination with immunotherapy agents, such as, e.g., checkpoint inhibitors, and may be useful in diagnostic tests as well.

These results show that relacorilant at dosages up to 400 mg/day demonstrated clinical improvement in hyperglycemia and hypertension, and also demonstrated improvement in other endpoints related to cortisol excess. Relacorilant was generally well tolerated. Thus, relacorilant offers clinical benefits of potent glucocorticoid modulation without undesirable anti-progesterone or mineralocorticoid (due to cortisol increase) mediated effects.

GR Antagonism is a Clinically Validated Treatment for Cushing Syndrome

In the first study with relacorilant in patients with Cushing syndrome (CORT125134-451; NCT02804750), a total of 35 patients were enrolled at 19 centers in the United States, Italy, United Kingdom, Hungary, and Netherlands.

Twenty-eight patients (80%) had an adrenocorticotropin hormone (ACTH)-dependent source of Cushing syndrome (either pituitary or ectopic) and 7 patients (20%) had an adrenal source of Cushing syndrome. The efficacy of the drug in Cushing syndrome was assessed based on the improvement of morbidities associated with excess cortisol activity, e.g. hyperglycaemia, hypertension, cognitive dysfunction, depression, poor quality of life, hypercoagulopathy and obesity. (A morbidity associated with excess cortisol, e.g., associated with hypercortisolemia, Cushing's syndrome, Cushing's disease, etc., is also termed a "comorbidity".)

Consistent with the expected dose effect, $2/13$ (15.4%) patients with hyperglycaemia treated with doses up to 200 mg and half of the patients ($6/12$) with hyperglycaemia treated with doses up to 400 mg showed robust evidence of glycemic improvement. Response was based on ≥0.5% reduction of HbA1c associated with reduction or discontinuation of diabetes medications or clinically significant reduction (≥50 mg/dL decrease) or normalisation of the 2-hour glucose measurement from an oral glucose tolerance test (OGTT). Among patients with uncontrolled hypertension, $5/12$ (41.7%) of the patients receiving doses up to 200 mg daily, and $7/11$ (63.6%) of the patients receiving doses up to 400 mg daily showed a clinically significant improvement (≥5 mmHg reduction) in their 24-hour mean systolic and diastolic BP measured with 24-hour ambulatory blood pressure monitoring. These patients also showed clinically significant improvement in their nocturnal and daytime blood pressures. This clinical improvement was observed without any episodes of drug induced hypokalemia—a commonly seen adverse event in patients treated with either mifepristone or metyrapone. As expected, patients treated with relacorilant also demonstrated no adverse effects of progesterone receptor antagonism, an additional benefit over mifepristone.

Besides the improvement in hyperglycaemia and hypertension, generally observed within two weeks of achieving a therapeutic dose of relacorilant, significant improvements were also observed in a number of other cortisol-related comorbidities as seen in TABLE 2 below:

TABLE 2

Secondary endpoint improvements in patients with Cushing's syndrome

| Secondary endpoint | P-value |
|---|---|
| Cushing QoL Score | <0.005 |
| Cognitive tests (Trail Making Test Part A) | <0.005 |
| Cognitive tests (Trail Making Test Part B) | <0.0001 |
| Beck Depression Scale | <0.003 |
| Coagulopathy (Factor VIII) | <0.03 |
| Coagulopathy (Platelets) | <0.0001 |
| Coagulopathy (APTT) | <0.05 |
| Liver Function Tests (ALT, AST) | <0.002 |
| Fructosamine | <0.006 |
| Osteocalcin | <0.01 |
| Eosinophils | <0.007 |

Although greater weight loss is generally seen the longer the duration of treatment with GR antagonists, significant weight changes were observed within 3 months in half of the patients in the relacorilant study with an average weight loss of 2.2 kg in patients treated with doses up to 200 mg daily and 5.1 kg in patients treated with doses up to 400 mg daily.

Improvement/normalization of abnormally elevated coagulation factors caused by excess cortisol activity was observed as early as after one month of treatment with relacorilant. This is in contrast to what is observed after curative surgery for pituitary Cushing syndrome cases where coagulation factors start to decrease 3 months post-surgery and often remain elevated for at least 6 months post-surgery (Trementino et al., *Neuroendocrinology* 92 Suppl 1:55-59 (2010). Considering the high risk of thrombotic events in patients with active Cushing syndrome as well as following curative surgery, relacorilant might even be an option for pre-operative coagulation control of patients at high risk of peri- and post-operative thrombotic events.

In patients with adrenal Cushing syndrome, restoration of the suppressed hypothalamic pituitary adrenal (HPA) axis was observed in half of the cases, even in patients with severe Cushing syndrome who had previously been treated with metyrapone chronically. Restoration of the HPA axis, based on recovery of the ACTH secretion and in some cases restoration of the diurnal cortisol rhythm, was observed within 2 to 6 weeks of treatment with relacorilant. This is an important finding, and bears emphasis for at least two reasons: A) It shows the rapid beneficial effects of relacorilant in patients with cortisol excess. The recovery of the HPA axis following curative surgery typically takes several months and sometimes takes years; and B) It provides a marker for dose titration in a manner analogous to thyroid-stimulation hormone (TSH) in patients with hyperthyroidism or plasma renin activity in patients with primary aldosteronism.

The safety profile of relacorilant in patients with endogenous Cushing syndrome was also significantly better than that seen with mifepristone. Unlike mifepristone's adverse events related to progesterone receptor antagonism, no cases of drug induced vaginal bleeding were seen in the relacorilant study, even among patients who had previously developed vaginal bleeding while taking mifepristone. Equally important, no patients developed drug induced hypokalemia, even those who had developed hypokalemia while taking mifepristone. The most common treatment-emergent adverse events (TEAEs) were back pain, edema, headache, and nausea.

In the Phase 2 CORT125134-451 study with relacorilant, five patients being treated with other approved medical therapies were titrated off their medication and enrolled in the study. These patients had only partially responded or had developed adverse events to the other therapies. Two patients had been treated with metyrapone, two with ketoconazole and one with mifepristone. In both patients treated previously with metyrapone, relacorilant showed higher efficacy based on improvement in the primary endpoints, improved glucose control and hypertension, and secondary end points, including weight loss and recovery of the HPA axis. The patient who was treated previously with mifepristone had developed endometrial hypertrophy which completely resolved during treatment with relacorilant.

Relacorilant was rationally designed to be a selective GR antagonist and does not bind to other nuclear steroid hormone receptors. Relacorilant's GR selectivity and particularly its lack of binding to the progesterone receptor provides a significant safety advantage over mifepristone. There have been no reported instances with relacorilant to date of two common TEAS reported with mifepristone: vaginal bleeding or hypokalemia.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

I claim:

1. A method of treating a patient suffering from a symptom of hypercortisolemia, or a comorbidity thereof, the method comprising administering to said patient an effective amount of relacorilant, where relacorilant is ((R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone), which has the following structure:

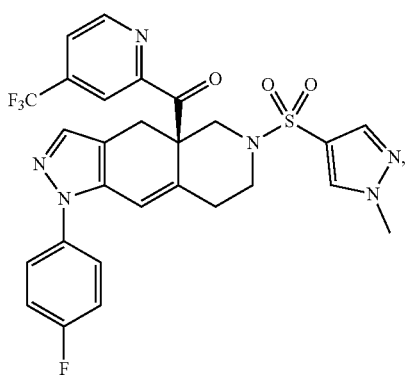

effective to treat said symptom or comorbidity of hypercortisolemia, wherein said symptom or comorbidity of hypercortisolemia is one or more of:

hyperglycemia, wherein said treatment is effective to a) lower the patient's $AUC_{glucose}$ by at least 15% as compared to the patient's baseline $AUC_{glucose}$ measured prior to treatment; b) decrease the patient's 2-hr oral glucose tolerance test (OGTT) glucose by at least 50 mg/dL as compared to the patient's baseline 2-hr OGTT glucose; c) decrease the patient's total daily insulin dose by at least 25% as compared to the patient's total daily insulin dose prior to treatment; d) decrease the patient's daily sulfonylurea dose by at least 50% as compared to the patient's total daily sulfonylurea dose prior to treatment, or e) decrease the patient's hemoglobin A1c (HbA1c) by at least 0.5% as compared to the patient's baseline HbA1c;

hypertension, wherein said treatment is effective to lower the patient's 24-hour mean systolic or 24-hour mean diastolic blood pressure by at least 5 millimeters of mercury (mmHg) as compared to the patient's baseline blood pressure measured prior to treatment;

a liver enzyme level, wherein said treatment is effective to lower patient alanine aminotransaminase (ALT) levels by at least 10.6 units per liter (U/L) or to lower patient aspartate amino transferase (AST) levels by at least 4.9 units per liter (U/L) as compared to the patient's baseline liver enzyme level measured prior to treatment;

a fructosamine level, wherein said treatment is effective to lower the patient's fructosamine level by at least 13.2 micromoles per liter (μmol/L) as compared to the patient's baseline fructosamine level measured prior to treatment;

a serum osteocalcin level, wherein said treatment is effective to increase the patient's serum osteocalcin level by at least 3 micrograms per liter (μg/L) as compared to the patient's baseline serum osteocalcin level measured prior to treatment;

a heartbeat interval, wherein said treatment is effective to reduce the patient's heartbeat aggregate QT interval by at least 13.6 milliseconds (msec) as compared to the patient's baseline heartbeat aggregate QT interval measured prior to treatment;

a blood coagulation measure, wherein a) said treatment is effective to improve a patient blood coagulation measure, wherein a) the treatment is effective to reduce the patient blood coagulation measure Factor VIII percent (%) by at least 18%; or b) the treatment is effective to increase the patient blood coagulation measure activated partial thromboplastin time (aPTT) by at least 1.45 seconds (sec); or c) the treatment is effective to improve an abnormal patient blood coagulation measure, wherein said improved abnormal patient blood coagulation measure is selected from a reduction in Factor IX % of at least 22% and a reduction in Factor X % of at least 18%; all as compared to the patient's corresponding baseline blood coagulation measure as measured prior to treatment;

a blood cell measure, wherein said treatment is effective to decrease the patient's platelet count by at least $68.8 \times 10^9$ per liter ($10^9$/L) or to increase the patient's absolute eosinophil count by at least $0.05 \times 10^9$/L as compared to the patient's baseline platelet count or absolute eosinophil count, respectively, as measured prior to treatment;

a proadrenocorticotropic hormone (proACTH) and pro-opiomelanocortin (POMC) level, wherein said treatment is effective to increase the patient's proACTH and POMC level by at least 7.9 picomoles per liter (pmol/L) as compared to the patient's baseline proACTH and POMC level as measured prior to treatment;

a poor quality of life measure in a Cushing's syndrome patient, wherein said treatment is effective to improve the patient's quality of life as measured by an increase of at least 6.9 in the patient's Cushing Quality of Life (QOL) Score as compared to the patient's baseline Cushing QOL Score as measured prior to treatment;

cognitive dysfunction in a Cushing's syndrome patient, wherein said treatment is effective to improve patient cognition as measured by a reduction of at least 4.1 seconds in total time to complete a Trail Making cognitive test part A, or as measured by a reduction of at least 24.7 seconds in total time to complete a Trail Making cognitive test part B, as compared to the patient's baseline cognition as measured by said cognitive tests prior to treatment;

a suppressed hypothalamic pituitary adrenal (HPA) axis, wherein said treatment is effective to restore the HPA axis, wherein said restoration of the HPA axis is indicated by recovery of ACTH secretion in the patient, or restoration of diurnal cortisol rhythm in the patient, or both; and a patient depression measure, as measured by the Beck Depression Inventory total score (BDI-II Total Score), wherein said treatment is effective to reduce the patient's BDI-II Total Score by at least 4.2 as compared to the patient's baseline BDI-II Total Score as measured prior to treatment;

whereby the patient suffering from a symptom or comorbidity of hypercortisolemia is treated and the symptom or comorbidity is treated.

2. The method of claim 1, wherein said symptom or comorbidity thereof is hyperglycemia, wherein said treatment is effective to treat said hyperglycemia by one or more of i) decreasing the patient's 2-hr oral glucose tolerance test (OGTT) glucose by at least 50 mg/dL as compared to the patient's baseline 2-hr OGTT glucose; ii) decreasing the patient's total daily insulin dose by at least 25% as compared to the patient's total daily insulin dose prior to treatment; or iii) decreasing the patient's daily sulfonylurea dose by at least 50% as compared to the patient's total daily insulin dose prior to treatment.

3. The method of claim 1, wherein said symptom or comorbidity thereof is hyperglycemia, wherein said treatment is effective to lower the patient's hemoglobin A1c (HbA1c) by at least 0.5% as compared to the patient's baseline HbA1c measured prior to treatment.

4. The method of claim 1, wherein said symptom or comorbidity thereof is hyperglycemia, wherein said treatment is effective to lower the patient's $AUC_{glcose}$ by at least 15% as compared to the patient's baseline $AUC_{glucose}$ measured prior to treatment.

5. The method of claim 1, wherein said symptom or comorbidity thereof is hypertension, wherein said treatment is effective to lower the patient's 24-hour mean systolic or 24-hour mean diastolic blood pressure by at least 5 millimeters of mercury (mmHg) as compared to the patient's baseline blood pressure measured prior to treatment.

6. The method of claim 1, wherein said symptom or comorbidity thereof is a heartbeat interval, wherein said treatment is effective to reduce the patient's heartbeat aggregate QT interval by at least 13.6 msec as compared to the patient's baseline heartbeat aggregate QT interval measured prior to treatment.

7. The method of claim 1, wherein said symptom or comorbidity thereof is a liver enzyme level, wherein said treatment is effective to lower patient alanine aminotransferase (ALT) levels by at least 10.6 units per liter (U/L) or to lower patient aspartate aminotransferase (AST) liver enzyme levels by at least 4.9 units per liter (U/L), or both, as compared to the patient's baseline ALT or AST liver enzyme level, respectively, as measured prior to treatment.

8. The method of claim 1, wherein said symptom or comorbidity thereof is a fructosamine level, wherein said treatment is effective to lower the patient's fructosamine level by at least 13.2 micromoles per liter (µmol/L) as compared to the patient's baseline fructosamine level measured prior to treatment.

9. The method of claim 1, wherein said symptom or comorbidity thereof is an osteocalcin level, wherein said treatment is effective to increase the patient's serum osteocalcin level by at least 3 micrograms per liter (µg/L) as compared to the patient's baseline osteocalcin level measured prior to treatment.

10. The method of claim 1, wherein said symptom or comorbidity thereof is a blood coagulation factor level, wherein said treatment is effective to improve a patient blood coagulation factor level, wherein said improved patient blood coagulation factor level is selected from a reduction in Factor VIII percent (%) of at least 18%, a reduction in an abnormal Factor IX % level of at least 22%, or a reduction in an abnormal Factor X % level of at least 18%, as compared to the patient's baseline Factor VIII, Factor IX, or Factor X level, respectively, as measured prior to treatment.

11. The method of claim 1, wherein said symptom or comorbidity thereof is a blood coagulation measure, wherein said treatment is effective to increase the patient's activated partial thromboplastin time (aPTT) by at least 1.45 seconds (sec) as compared to the patient's baseline aPTT as measured prior to treatment.

12. The method of claim 1, wherein said symptom or comorbidity thereof is a blood cell measure selected from an abnormal eosinophil measure or abnormal platelet count, wherein said treatment is effective to increase the patient's absolute patient eosinophil count by at least $0.05 \times 10^9$/L or decrease the patient's platelet count by at least $68.8 \times 10^9$/L as compared to the patient's baseline eosinophil measure or abnormal platelet count, respectively, as measured prior to treatment.

13. The method of claim 1, wherein said symptom or comorbidity thereof is a proadrenocorticotropic hormone and pro-opiomelanocortin (POMC and proACTH) level, wherein said treatment is effective to increase the patient's POMC and proACTH level by at least 7.9 picomoles per liter (pmol/L) as compared to the patient's baseline POMC and proACTH level as measured prior to treatment.

14. The method of claim 1, wherein said symptom or comorbidity thereof is poor quality of life in a Cushing's syndrome patient, wherein said treatment is effective to improve patient quality of life as measured by an increase of at least 6.9 in the Cushing Quality of Life Score (QOL), as compared to the patient's baseline Cushing QOL Score measured prior to treatment.

15. The method of claim 1, wherein said symptom or comorbidity thereof is cognitive dysfunction in a Cushing's syndrome patient, wherein said treatment is effective to improve patient cognition as measured by a reduction of at least 4.1 seconds in total time to complete a Trail Making cognitive test part A, or as measured by a reduction of at least 24.7 seconds in total time to complete a Trail Making cognitive test part B, as compared to the patient's baseline cognition as measured by said cognitive tests prior to treatment.

16. The method of claim 1, wherein said symptom or comorbidity thereof is a suppressed hypothalamic pituitary adrenal (HPA) axis, wherein said treatment is effective to restore the HPA axis, wherein said restoration of the HPA axis is indicated by recovery of ACTH secretion in the patient, or restoration of diurnal cortisol rhythm in the patient, or both.

17. The method of claim 1, wherein said symptom or comorbidity thereof is depression, as measured by the Beck Depression Inventory total score (BDI-II Total Score), wherein said treatment is effective to reducethe patient's BDI-II Total Score by at least 4.2 as compared to the patient's baseline depression as so BDI-II Total Score measured prior to treatment.

18. The method of claim 1, wherein said relacorilant is orally administered.

19. The method of claim 1, wherein said relacorilant is administered without food.

20. The method of claim 1, wherein said relacorilant is administered with food.

21. The method of claim 1, wherein said relacorilant is administered at a daily dose selected from 10 milligrams per day (mg/day), 20 mg/day, 30 mg/day, 40 mg/day, 50 mg/day, 100 mg/day, 150 mg/day, 200 mg/day, 250 mg/day, 300 mg/day, 350 mg/day, 400 mg/day, and 500 mg/day.

22. The method of claim 1, wherein said relacorilant is administered daily for a period of time selected from 1 week, 2 weeks, 3 weeks, 4 weeks, 5 weeks, 6 weeks, 7 weeks, 8 weeks, 10 weeks, 11 weeks, 12 weeks, and 20 weeks.

\* \* \* \* \*

UNITED STATES PATENT AND TRADEMARK OFFICE
CERTIFICATE OF CORRECTION

PATENT NO. : 11,058,670 B2  
APPLICATION NO. : 16/797421  
DATED : July 13, 2021  
INVENTOR(S) : Andreas Moraitis Page 1 of 1

It is certified that error appears in the above-identified patent and that said Letters Patent is hereby corrected as shown below:

In the Claims

In Column 41, Line 16, Claim 1, delete "A 1c" and replace with --A1c--

In Column 42, Line 56, Claim 4, delete "$AUC_{glcose}$by" and replace with --$AUC_{glucose}$ by--

In Column 42, Line 57, Claim 4, delete "$AUC_{glucose}$mea-" and replace with --$AUC_{glucose}$ mea- --

In Column 44, Line 9, Claim 14, delete "(QOL),"  and replace with --(QOL)--

In Column 44, Line 33, Claim 17, delete "reducethe" and replace with --reduce the--

In Column 44, Line 35, Claim 17, delete "depression as so"

Signed and Sealed this  
Eighteenth Day of January, 2022

Drew Hirshfeld  
*Performing the Functions and Duties of the*  
*Under Secretary of Commerce for Intellectual Property and*  
*Director of the United States Patent and Trademark Office*